(12) United States Patent
Slabas et al.

(10) Patent No.: US 6,455,688 B1
(45) Date of Patent: Sep. 24, 2002

(54) PLANT GENE SPECIFYING ACETYL COENZYME A CARBOXYLASE AND TRANSFORMED PLANTS CONTAINING SAME

(75) Inventors: Antoni Ryzsard Slabas, High Shincliff; Kieran Michael Elborough, Hartlepool; Simon William Jonathan Bright, Marlow; Phillip Anthony Fentem, Walkington, all of (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 08/737,109

(22) PCT Filed: Apr. 21, 1994

(86) PCT No.: PCT/GB94/00846
§ 371 (c)(1),
(2), (4) Date: Oct. 21, 1996

(87) PCT Pub. No.: WO95/29246
PCT Pub. Date: Apr. 21, 1994

(51) Int. Cl.[7] ............ C07H 21/04; C12N 15/82
(52) U.S. Cl. ............ 536/23.6; 435/69.1; 800/281
(58) Field of Search .................. 800/205, 250, 800/298, 278, 281, 286, 287; 435/69.1, 418, 419; 536/23.6

(56) References Cited

FOREIGN PATENT DOCUMENTS

WO 93/11243 * 6/1993

OTHER PUBLICATIONS

Elborough et al. Plant Mol Biol 24: 21–34, Jan. 1994.*
Elborough et al, J. Cell Biochem Suppl. 18A, p. 113, Jan. 1994.*
Database sequence accession No. Z23038, Jan. 1995.*
Database sequence accession No. S42660, Jan. 1995.*

* cited by examiner

*Primary Examiner*—Elizabeth F. McElwain
(74) *Attorney, Agent, or Firm*—Morgan, Lewis & Bockius LLP

(57) ABSTRACT

DNA sequence of an acetyl Coenzyme A carboxylase from plants are inserted into the genome of plants in sense or antisense orientation in order to inhibit expression of the gene product of the endogenous ACCase gene, resulting in reduced conversion of the enzyme's substrate, acetyl Coenzyme A, to fatty acid synthesis, leaving the substrate available for diversion into other biosynthesis pathways. One such diversion may be accomplished by providing the plant genome with genes specifying the synthesis of polyhydroxyalkanoate polymers.

17 Claims, 29 Drawing Sheets

FIG. 3

AA sequencing from Wheat ACCase    MATNGVE?LTVSDDLEG
pK111 deduced AA sequence        81MATNGVVHLTVSDDLEG AA sequencing from Wheat ACCase    LGGIPVGVIAVETQT?DQ
pK111 deduced AA sequence        181LGGIPVGXIAVETQTMMQ AA sequencing from Wheat ACCase    NVLEPQGHL
pK111 deduced AA sequence        319NVXEXQGLI AA sequencing from Wheat ACCase    SIEARKKQLLPLYTQIAIRF
pK111 deduced AA sequence        372SIEPRKKQLLPLYTQIAVRF

FIG. 4

DNA sequence     1926 b.p.    GAGAACATACAT ... *TCCAGTTTTTT   linear

```
1/1                                     31/11
GAG AAC ATA CAT GGA AGT GCT GCT ATT GCC AGT GCC TAT TCT AGG GCC TAT GAG GAG ACA
 E   N   I   H   G   S   A   A   I   A   S   A   Y   S   R   A   Y   E   E   T
   R   T   Y   M   E   V   L   L   L   P   V   P   I   L   G   P   M   R   R   H
     E   H   T   W   K   C   C   Y   C   Q   C   L   F   *   G   L   *   G   D   I
61/21                                   91/31
TTT ACG CTT ACA TTT GTG ACT TGA CGG ACT GTT GGA ATA GGA GCA TAT CTT GCT CGA CTT
 F   T   L   T   F   V   T   *   R   T   V   G   I   G   A   Y   L   A   R   L
   L   R   L   H   *   L   D   G   L   L   E   *   E   H   I   L   L   D   L
     Y   A   Y   I   C   D   L   T   D   C   W   N   R   S   I   S   C   S   T   W
121/41                                  151/51
GGC ATA CGG TGC ATA CAG CGT ACT GAC CAG CCC ATT ATC CTA ACC GGG TTC TCT GCT TTG
 G   I   R   C   I   Q   R   T   D   Q   P   I   I   L   T   G   F   S   A   L
   A   Y   G   A   Y   S   V   L   T   S   P   L   S   *   P   G   S   L   L   *
     H   T   V   H   T   A   Y   *   P   A   H   Y   P   N   R   V   L   C   F   E
181/61                                  211/71
AAC AAG CTT CTT GGC CGG GAA GTG TAC AGC TCC CAC ATG CAG TTG GGT GGC CCC AAA ATT
 N   K   L   L   G   R   E   V   Y   S   S   H   M   Q   L   G   G   P   K   I
   T   S   F   L   A   G   K   C   T   A   P   T   C   S   W   V   A   P   K   L
     Q   A   S   W   P   G   S   V   Q   L   P   H   A   V   G   W   P   Q   N   Y
241/81                                  271/91
ATG GCG ACA AAC GGT GTT GTC CAT CTG ACA GTT TCA GAT GAC CTT GAA GGT GTG TCT AAT
 M   A   T   N   G   V   V   H   L   T   V   S   D   D   L   E   G   V   S   N
   W   R   Q   T   V   L   S   I   *   Q   F   Q   M   T   L   K   V   C   L   I
     G   D   K   R   C   C   P   S   D   S   F   R   *   P   *   R   C   V   *   Y
301/101                                 331/111
ATA TTG AGG TGG CTC AGC TAT GTT CCT GCC AAC ATT GGT GGA CCT CTT CCT ATT ACA AAA
 I   L   R   W   L   S   Y   V   P   A   N   I   G   G   P   L   P   I   T   K
   Y   *   G   G   S   A   M   F   L   P   T   L   V   D   L   F   L   L   Q   N
     I   E   V   A   Q   L   C   S   C   Q   H   W   W   T   S   S   Y   Y   K   I
361/121                                 391/131
TCT TTG GAC CCA CCT GAC AGA CCC GTT GCA TAT ATC CCT GAG AAT ACA TGT GAT CCT CGT
 S   L   D   P   P   D   R   P   V   A   Y   I   P   E   N   T   C   D   P   R
   L   W   T   H   L   T   D   P   L   H   I   S   L   R   I   H   V   I   L   V
     F   G   P   T   *   Q   T   R   C   I   Y   P   *   E   Y   M   *   S   S   C
```

FIG. 4
CONTINUED

```
421/141                                  451/151
GCA GCC ATC AGT GGC ATT GAT GAT AGC CAA GGG AAA TGG TTG GGG GGC ATG TTC GAC AAA
 A   A   I   S   G   I   D   D   S   Q   G   K   W * L   G   G   M   F   D   K
   Q   P   S   V   A   L   H   I   A   K   G   N   W   G   A   C   S   T   K
     S   H   Q   W   H   *   *   *   P   R   E   M   V   G   G   H   V   R   Q   R
481/161                                  511/171
GAC AGT TTT GTG GAG ACA TTT GAA GGA TGG GCG AAG TCA GTA GTT ACT GGC AGA GCG AAA
 D   S   F   V   E   T   F   E   G   W   A   K   S   V   V   T   G   R   A   K
   T   V   L   W   R   H   L   K   D   G   R   S   Q   *   L   L   A   E   R   N
     Q   F   C   G   D   I   *   R   M   G   E   V   S   S   Y   W   Q   S   E   T
541/181                                  571/191
CTC GGA GGG ATT CCG GTG GGT GT* ATA GCT GTG GAG ACA CAG ACT ATG ATG CAG CTC ATC
 L   G   G   I   P   V   G   X   I   A   V   E   T   Q   T   M   M   Q * L   I
   S   E   G   F   R   W   V   X   *   L   W   R   H   R   L   *   C   S   S   S
     R   R   D   S   G   G   C   X   S   C   G   D   T   D   Y   D   A   A   H   P
601/201                                  631/211
CCT GCT GAT CCA GGG CAG CTT GAT TCC CAT GAG CGG TCT GTT CCT CGT *CT GGG CAA GT*
 P   A   D   P   G   Q   L   D   S   H   E   R   S   V   P   R   X   G   Q   X
   L   L   I   Q   G   S   L   I   P   M   S   G   L   F   L   X   L   G   K   X
     C   *   S   R   A   A   *   F   P   *   A   V   C   S   S   X   W   A   S   X
661/221                                  691/231
TGG TTT CCA *AT T*A *CT ACT AAG ACA GCT CAA GCA ATG CTG GAC TTC AAC CGT *AA GGA
 W   F   P   X   X   X   T   K   T   A   Q   A   M   L   D   F   N   R   X   G
   G   F   X   I   X   L   L   R   Q   L   K   Q   C   W   T   S   T   X   K   D
     V   S   X   X   X   Y   *   D   S   S   S   N   A   G   L   Q   P   X   R   I
721/241                                  751/251
TTA CCT CT* TTC ATC CTT GC* AAC TGG AGA GGC TTC T*T GGT GGG CAA AGA GAT CTT TTT
 L   P   X   F   I   L   X   N   W   R   G   F   X   G   G   Q   R   D   L   F
   Y   L   X   S   S   L   X   T   G   E   A   S   X   V   G   K   E   I   F   L
     T   S   X   H   P   C   X   L   E   R   L   X   W   A   K   R   S   F   *
781/261                                  811/271
AAA GGA ATC CTT CAG GCT GGG TCA ACA ATT GTT GAG AAC CTT AGG ACA TAC AAT CAG CCT
 K   G   I   L   Q   A   G   S   T   I   V   E   N   L   R   T   Y   N   Q   P
   K   E   S   F   R   L   G   Q   Q   L   L   R   T   L   G   H   T   I   S   L
     R   N   P   S   G   W   V   N   N   C   *   E   P   *   D   I   Q   S   A   C
```

FIG. 4
CONTINUED

```
841/281                                   871/291
GCC TTT GTA TAT ATC CCC AAG GCT GCA GAG CTA CGT GGA GGG GCT TGG GTC GTG ATT GAT
 A   F   V   Y   I   P   K   A   A   E   L   R   G   G   A   W   V   V   I   D
   P   L   Y   I   S   P   R   L   Q   S   Y   V   E   G   L   G   S   *   L   I
     L   C   I   Y   P   Q   G   C   R   A   T   W   R   G   L   G   R   D   *   *
901/301                                   931/311
AGC AAG ATA AAT CCA GAT CGA TTT GAG TTC TaT GCT GAG AGG ACT GCA AAG GGT AAT GTT
 S   K   I   N   P   D   R   F   E   F   Y   A   E   R   T   A   K   G   N   V
   A   R   *   I   Q   I   D   L   S   S   M   L   R   G   L   Q   R   V   M   F
     Q   D   K   S   R   S   I   *   V   L   C   *   E   D   C   K   G   *   C   S
961/321                                   991/331
CT* GAA CC* CAA GGG TTG ATT GA* ATC AA* TTC AGG TCA GAG GAA CTC CAA GAG TGC ATG
 X   E   X   Q   G   L   I   X   I   X   F   R   S   E   E   L   Q   E   C   M
   X   N   X   K   G   *   L   X   S   X   S   G   Q   R   N   S   K   S   A   W
     X   T   X   R   V   D   *   X   Q   X   Q   V   R   G   T   P   R   V   H   G
1021/341                                  1051/351
GGC AGG GTT GAC CCA GAA TTG ATA AAT CTG AAG GCA AAA CTC CTG GGA GCA AAG CAT GAC
 G   R   V   D   P   E   L   I   N   L   K   A   K   L   L   G   A   K   H   D
   A   G   L   T   Q   N   *   *   I   *   R   Q   N   S   W   E   Q   S   M   T
     Q   G   *   P   R   I   D   K   S   E   G   K   T   P   G   S   K   A   *   Q
1081/361                                  1111/371
AAT GGA AGT CTA TCT GAG TCA GAA TCC CTT CAG AAG AGC ATA GAA CCC CGG AAG AAA CAG
 N   G   S   L   S   E   S   E   S   L   Q   K   S   I   E   P   R   K   K   Q
   M   E   V   Y   L   S   Q   N   P   P   R   R   A   *   N   P   G   R   N   S
     W   K   S   I   *   V   R   I   P   S   E   E   H   R   T   P   E   E   T   V
1141/381                                  1171/391
TTG TTG CCT TTG TAT ACT CAA ATT GCG GTG CGG TTT GCT GAA TTG CAT GAC ACT TCC CTT
 L   L   P   L   Y   T   Q   I   A   V   R   F   A   E   L   H   D   T   S   L
   C   C   L   C   I   L   K   L   R   C   G   L   L   N   C   M   T   L   P   L
     V   A   F   V   Y   S   N   C   G   A   V   C   *   I   A   *   H   F   P   *
1201/401                                  1231/411
AGA ATG GCT *CT AAG GGT GTG ATT AAG AAG GTT GTA GAC TGG AAA GAT TCT AGG TCT TTC
 R   M   A   X   K   G   V   I   K   K   V   V   D   W   K   D   S   R   S   F
   E   W   X   L   R   V   *   L   R   R   L   *   T   G   K   I   L   G   L   S
     N   G   X   *   G   C   D   *   E   G   C   R   L   E   R   F   *   V   F   L
1261/421                                  1291/431
TTC TAC AAG AGA TTA CGG AGG AGG ATA TCC GAG GAC GTT CTT *CA AAG GAA ATT AGA GGT
 F   Y   K   R   L   R   R   R   I   S   E   D   V   L   X   K   E   I   R   G
   S   T   R   D   Y   G   G   G   Y   P   R   T   F   X   Q   R   K   L   E   V
     L   Q   E   I   T   E   E   D   I   R   G   R   S   X   K   G   N   *   R   C
```

FIG. 4
CONTINUED

```
1321/441                                      1351/451
GTA AGT GGC AAG CAG TTC TCT CAC CAA TCA GCA ATC GAG CTG ATC CAG AAA TGG TAC TTG
 V   S   G   K   Q   F   S   H   Q   S   A   I   E   L   I   Q   K   W   Y   L
   *   V   A   S   S   S   L   T   N   Q   Q   S   S   *   S   R   N   G   T   W
     K   W   Q   A   V   L   S   P   I   S   N   R   A   D   P   E   M   V   L   G
1381/461                                      1411/471
GCT TCT AAG GGA GCT GAA GCA GCA AGC ACT GAA TGG GAT GAT GAC GAT GCT TTT GTT GCC
 A   S   K   G   A   E   A   A   S   T   E   W   D   D   D   D   A   F   V   A
   L   L   R   E   L   K   Q   Q   A   L   N   G   M   M   T   M   L   L   L   P
     F   *   G   S   *   S   S   K   H   *   M   G   *   *   R   C   F   C   C   L
1441/481                                      1471/491
TGG AGG AAA AAC CCT GAA AAC TAC CAG GAG TAT ATC AAA GAA CTT AGG GCT CAA AGG GTA
 W   R   K   N   P   E   N   Y   Q   E   Y   I   K   E   L   R   A   Q   R   V
   G   G   K   T   L   K   T   T   R   S   I   S   K   N   L   G   L   K   G   Y
     E   G   K   P   *   K   L   P   G   V   Y   Q   R   T   *   G   S   K   G   I
1501/501                                      1531/511
TCT CAG TTG CTC TCA GAT GTT GCA GAC TCC AGT CCA GAT CTA GAA GCC TTG CCA CAG GGT
 S   Q   L   L   S   D   V   A   D   S   S   P   D   L   E   A   L   P   Q   G
   L   S   C   S   Q   M   L   Q   T   P   V   Q   I   *   K   P   C   H   R   V
     S   V   A   L   R   C   C   R   L   Q   S   R   S   R   S   L   A   T   G   S
1561/521                                      1591/531
CTT TCT ATG CTA CTA GAG AAG ATG GAT CCC TCA AGG AGA GCA CAG TTT GTT GAG GAA GTC
 L   S   M   L   L   E   K   M   D   P   S   R   R   A   Q   F   V   E   E   V
   F   L   C   Y   *   R   R   W   I   P   Q   G   E   H   S   L   L   R   K   S
     F   Y   A   T   R   E   D   G   S   L   K   E   S   T   V   C   *   G   S   Q
1621/541                                      1651/551
AAG AAA GTC CTT AAA TGA TCA GAT GAT ACC AAC GCA TCC AAT TCA GAA TGT GCA TGA TAT
 K   K   V   L   K   *   S   D   D   T   N   A   S   N   S   E   C   A   *   Y
   R   K   S   L   N   D   Q   M   I   P   T   H   P   I   Q   N   V   H   D   I
     E   S   P   *   M   I   R   *   Y   Q   R   I   Q   F   R   M   C   M   I   S
1681/561                                      1711/571
CGG TTT CTC TTG AAG TAC ATA TAT AGA *GG ATA CTA TTC GGC TGT AAC CGA CCA TAG CTG
 R   F   L   L   K   Y   I   Y   R   X   I   L   F   G   C   N   R   P   *   L
   G   F   S   *   S   T   Y   I   X   G   Y   Y   S   A   V   T   D   H   S   *
     V   S   L   E   V   H   I   *   X   D   T   I   R   L   *   P   T   I   A   D
```

FIG. 4
CONTINUED

```
1741/581                                        1771/591
ATC TGA GTC AAC CAT TAT TTT GTA AAA CTT TTT TGC GGT CTT CTC TGT TAT TCG AGG CAA
 I   *   V   N   H   Y   F   V   K   L   F   C   G   L   L   C   Y   S   R   Q
  S   E   S   T   I   I   L   *   N   F   F   A   V   F   S   V   I   R   G   K
   L   S   Q   P   L   F   C   K   T   F   L   R   S   S   L   L   F   E   A   K
1801/601                                        1831/611
AAC TTG TTT TCG GAC GGC TCC GAA TGG TTG ATG AGT GTA GTT GGA AAA AAA GCG GCC GGA
 N   L   F   S   D   G   S   E   W   L   M   S   V   V   G   K   K   A   A   G
  T   C   F   R   T   A   P   N   G   *   *   V   *   L   E   K   K   R   P   E
   L   V   F   G   R   L   R   M   V   D   E   C   S   W   K   K   S   G   R   N
1861/621                                        1891/631
ATT *CT GCA GCC CGG GGG ATC C*C TAG TTC TAG AGC GGC CGC ACC GGG TTG GAG *TC CAG
 I   X   A   A   R   G   I   X   *   F   *   S   G   R   T   G   L   E   X   Q
  X   L   Q   P   G   G   S   X   S   S   R   A   A   A   P   G   W   X   S   S
   X   C   S   P   G   D   X   L   V   L   E   R   P   H   R   V   G   X   P   V
1921/641
TTT TTT
 F   F
  F
   F
```

FIG. 6A

```
           10          20          30          40          50          60          70          80
  1 ARGRNSLIYH SITKKGPLHG TQINDQYKPL GYLDRQRLAA RRSNTTYCYD FPLAFETALE QFGHYNNREL RNHARVLLSV
 81 LKSLYSPISE GTSLMPVERS PGLNEFGMVA WSLEMSTPEF PMGRKLLIVA NDVTFKAGSF GPREDAFFLA VTELACPKKL
161 PLIYLAPNSG ARLGVAEEIK ACFKVGWSDE VSPENGFQYI YLSPEDHARI GSSVIAHEIK LPSGETRWVI DTIVGKEDGI
241 GVENLTGSGP IAGAYSRAYN ETFTLTFVSG RTVGIGAYLA PLGMRCIQRL DQPIILTGFS TLNKLLGREV YSSHMQLGGP
321 KIMGTNGVVH LTVSDDLEGV SAILDWLSYI PAYVGGPLPV LAPLDPPDRT VEYVPENSCD PRAAIAGVND NTGKWLGGIF
401 DKNSFIETLE GWARTVVTGR AKLGGIPVGV VAVETQTVMQ IIPADPGQLD SHERVVPQAG QVWFPDSAGK TAQALMDFTR
481 KSFHCLSLRT GEGFQVGREI FSKEYFRQVA TIVENLRTYR QPVFVYIPKM GELRGGAWVV VDSQINSDYV EMYADETARG
561 NVLEPEGTIE IKFRTKEMLE CMGRLDPKLI DLKARLQDPN QSEAYTNIEL LQQIKAREK LLLPVYIQIA TKFAELHDTS
641 MRMTAKGVIK MCVEWIGSRS FFYKKLNRRI AENSLVKNVR EASGDDLSYK SAMGLIQDWF SKSDIPKGKE EAWTDDQVFF
721 TWKDNVSNYE LNLSELRPQK LLNPTCRDWK FRRIYRRCHK DLPIF 765
```

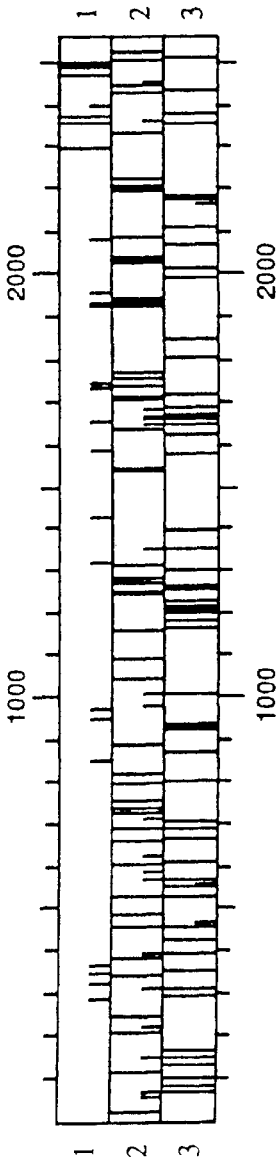

FIG. 6B

```
GCACGAGGGAGAAACAGTTTGATTTACCACTCAATTACCAAGAAGGGACCTTTGCATGGAA
CCCAAATCAATGATCAATATAAGCCACTGGGATATCTTGACAGGCAACGTCTAGCCGCAAG
GAGGAGTAACACTACATATTGCTATGACTTCCCGTTGGCATTTGAGACAGCCTTGGAGCAGT
TTGGGCATTACAACAACCGGGAGTTAAGAAACCATGCAAGGGTACTCTTATCAGTGCTAAA
GAGCTTGTATTCTCCAATTTCAGAAGGTACATCTCTTATGCCAGTTGAAAGATCACCGGGTC
TCAATGAGTTTGGAATGGTGGCCTGGAGCCTAGAGATGTCGACTCCTGAGTTTCCTATGGG
ACGGAAGCTTCTCATAGTCGCCAATGATGTCACCTTCAAAGCTGGTTCTTTTGGTCCTAGA
GAGGACGCGTTTTTCCTTGCCGTGACTGAACTCGCATGTCCCAAGAAGCTTCCCTTGATTTA
CTTGGCACCAAATTCTGGTGCCAGACTCGGAGTAGCTGAAGAAATCAAAGCCTGCTTTAAA
GTTGGATGGTCGGATGAAGTTTCCCCCGAAAATGGTTTTCAGTATATATACCTAAGCCCTGA
AGACCATGCAAGGATTGGATCATCTGTCATTGCGCACGAAATAAAGCTCCCTAGTGGGGAA
ACAAGGTGGGTGATTGATACAATCGTTGGTAAAGAAGATGGTATTGGTGTAGAGAATCTAA
CCGGAAGTGGGCCAATAGCGGGCGCTTACTCGAGGGCATACAACGAAACATTTACTTTGAC
CTTTGTTAGTGGAAGAACGGTAGGAATTGGTGCTTACCTTGCCCCCCTTGGTATGCGGTGTA
TACAGAGACTTGACCAGCCGATCATATTGACTGGCTTTTCTACGCTCAACAAGTTACTTGGG
CGTGAGGTCTATAGCTCTCACATGCAACTTGGTGGCCCGAAAATCATGGGCACAAATGGTGT
TGTTCATCTTACAGTCTCAGATGATCTCGAAGGTGTATCAGCGATTCTCGACTGGCTGAGCT
ACATTCCTGCTTACGTTGGTGGTCCTCTTCCTGTTCTTGCCCCGTTAGACCCACCGGACAGAA
CCGTGGAGTACGTTCCAGAGAACTCTTGCGACCCGCGAGCTGCTATAGCTGGGGTTAACGA
CAATACCGGTAAATGGCTTGGCGGTATCTTTGATAAAAATAGCTTTATTGAGACTCTTGAAG
GCTGGGCAAGAACGGTAGTGACTGGTAGAGCTAAACTAGGGGGAATACCTGTAGGAGTTG
TTGCGGTTGAGACACAGACAGTAATGCAGATCATCCCAGCAGATCCAGGACAGCTCGACTC
TCATGAAAGAGTGGTTCCACAGGCAGGGCAAGTCTGGTTTCCTGATTCTGCGGGCAAGACA
GCTCAAGCGCTCATGGATTTCACAAGGAAGAGCTTCCATTGTTTATCCTTGCGAACTGGAG
AGGGTTTTCAGGTGGGCAGAGAGATCTTTTCGAAGGAATACTTCAGGCAGGTTGCGACTAT
TGTAGAAAATCTGAGAACGTATCGGCAGCCAGTGTTTGTGTACATCCCTAAGATGGGAGAG
TTGCGAGGTGGAGCGTGGGTTGTTGTTGATAGCCAAATAAATTCAGATTATGTTGAAATGT
ATGCTGATGAAACTGCTAGGGGGAATGTGCTTGAGCCAGAAGGAACGATAGAGATAAAAT
TTAGAACGAAAGAGATGTTAGAGTGCATGGGAAGGTTAGACCCGAAGCTAATCGATCTCAA
AGCAAGACTGCAAGATCCCAACCAAAGTGAGGCTTATACAAATATCGAGCTCCTCCAGCAA
CAGATTAAAGCCCGAGAGAAGCTTCTCTTACCAGTTTATATCCAAATCGCCACCAAATTTGC
GGAACTTCACGATACTTCCATGAGAATGACTGCCAAAGGAGTGATCAAAATGTGTGTGGAG
TGGATCGGCTCGAGGTCCTTCTTCTATAAGAAGCTCAACCGGAGAATTGCTGAGAACTCTC
TTGTGAAAAACGTAAGAGAAGCTTCAGGAGACGACTTATCGTATAAATCTGCAATGGGTTT
AATTCAGGATTGGTTCTCCAAATCTGACATTCCAAAGGGGAAAGAAGAAGCTTGGACAGAC
GACCAAGTGTTCTTTACATGGAAGGACAACGTTAGTAACTACGAGTTGAATCTGAGCGAAT
TGAGACCGCAGAAACTGTTGAACCCAACTTGCAGAGATTGGAAATTCCGTCGGATCTATCG
GCGCTGCCACAAGGACTTGCCAATCTTCTAAACAAGGTGGAGCCTTCAAGAAGAGAAGAGC
TTGTTGAAGCGCTACGAAAAGTGTTAGGTTGATGTACAAGAGGTCAAGCTTGTGACCCGAG
AAAGATGGTCCTTTGGTGTTGCTTGTGTCCTACGGTGAAAGAAGCTAGTTGGAAATTAGAT
GTGGTCTTTCTTTCTTAAATGTGTTGGCCCGAGCTGTAAATGTTGTTGTAGCGTATAAGTGA
GAATTGCGTAATAATTTATTCAAC
```

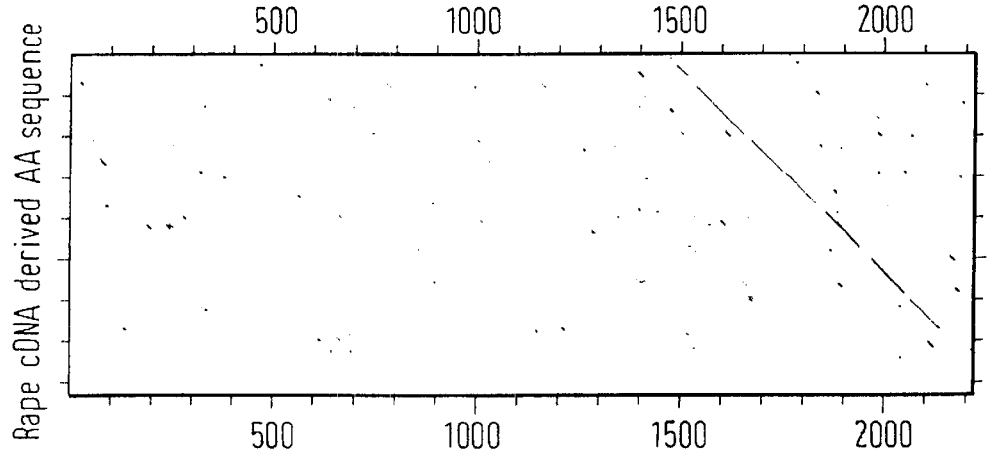
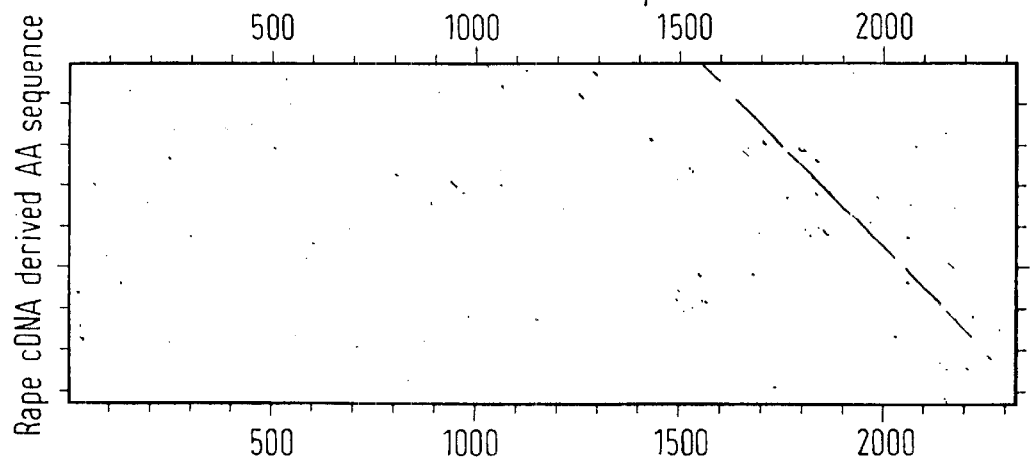
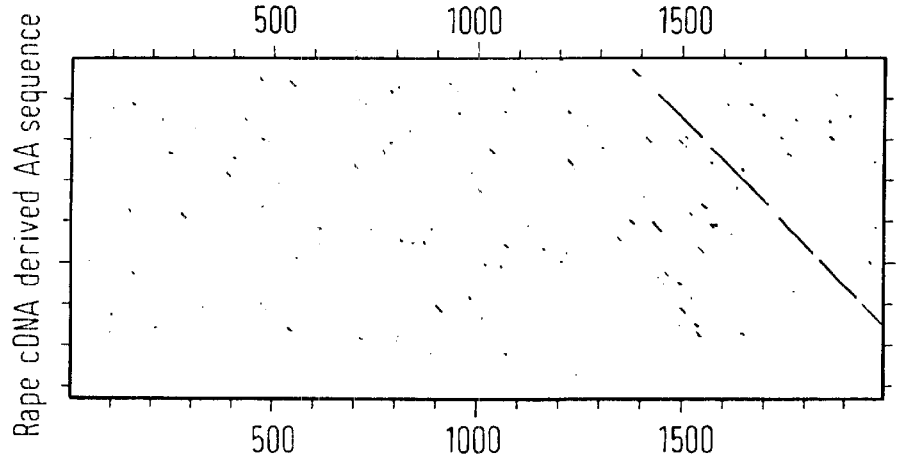
FIG. 7

FIG. 8

```
1/1                                            31/11
CTC TCT GGC AAA TCC CTG GTA TAA TCT ACG TCC TTA TTT CTT ACA GGC AGC GGT TCC TCT
 L   S   G   K   S   L   V   *   S   T   S   L   F   L   T   G   S   G   S   S
  S   L   A   N   P   W   Y   N   L   R   P   Y   F   L   Q   A   A   V   P   L
   L   W   Q   I   P   G   I   I   Y   V   L   I   S   Y   R   Q   R   F   L   F
61/21                                          91/31
TCT TTA TCC ATG CAC ACG AAT AAT GTA CTG TCT GTT TCT CTT TAA TTT CGT AGA GAT AAG
 S   L   S   M   H   T   N   N   V   L   S   V   S   L   *   F   R   R   D   K
  L   Y   P   C   T   R   I   M   Y   C   L   F   L   F   N   F   V   E   I   R
   F   I   H   A   H   E   *   C   T   V   C   F   S   L   I   S   *   R   *   D
121/41                                         151/51
ACG GTT CTA TGG AAT AGA ACA TGG TGG AGG TTA TGA TTC TTG GCG AAA AAC ATC TGT TGT
 T   V   L   W   N   R   T   W   W   R   L   *   F   L   A   K   N   I   C   C
  R   F   Y   G   I   E   H   G   G   G   Y   D   S   W   R   K   T   S   V   V
   G   S   M   E   *   N   M   V   E   V   M   I   L   G   E   K   H   L   L   *
181/61                                         211/71
AGC CTT CCC TTT TGA TTT TGA TAA AGC TCA ATC TAT AAG GCC AAA AGG TCA TTG TGT GGC
 S   L   P   F   *   F   *   *   S   S   I   Y   K   A   K   R   S   L   C   G
  A   F   P   F   D   F   D   K   A   Q   S   I   R   P   K   G   H   C   V   A
   P   S   L   L   I   L   I   K   L   N   L   *   G   Q   K   V   I   V   W   L
241/81                                         271/91
TGT ACG TGT GAC AAG TGA GGt aTC CTG ATG ACG GGT TCA AAC CAA CCA GCG GTA GAG TTC
 C   T   C   D   K   *   G   I   L   M   T   G   S   N   Q   P   A   V   E   F
  V   R   V   T   S   E   V   S   *   *   R   V   Q   T   N   Q   R   *   S   S
   Y   V   *   Q   V   R   Y   P   D   D   G   F   K   P   T   S   G   R   V   Q
301/101                                        331/111
AGG TAA TGT GAT ATC TGT GGA ATG CAA AGT GAA AGT TCA TTC ACT GAG AAA CTC TGT GGG
 R   *   C   D   I   C   G   M   Q   S   E   S   S   F   T   E   E   L   C   G
  G   N   V   I   S   V   E   C   K   V   K   V   H   S   L   R   N   S   V   G
   V   M   *   Y   L   W   N   A   K   *   K   F   I   H   *   G   T   L   W
361/121                                        391/131
GTA ACA CTT GTA TGA ACT TGC AAC AGG aGT TGA GTT TTA AGA GCA AGC CAA ATG TGT GGG
 V   T   L   V   *   T   C   N   R   S   *   V   L   R   A   S   Q   M   C   G
  *   H   L   Y   E   L   A   T   G   V   E   F   *   E   Q   A   K   C   V   G
   N   T   C   M   N   L   Q   Q   E   L   S   F   K   S   K   P   N   V   W   A
421/141                                        451/151
CGT ACT TCT CTG TCA AGG TAA TTT ATA TCT ATA GaG aCt ctg cta tat aag tgt ttc aca
 R   T   S   L   S   R   *   F   I   S   I   E   T   L   L   Y   K   C   F   T
  V   L   L   C   Q   G   N   L   Y   L   *   R   L   C   Y   I   S   V   S   Q
   Y   F   S   V   K   V   I   Y   I   Y   R   D   S   A   I   *   V   F   H   N
481/161                                        511/171
atg *tt taa ttt t*c ggc tac ttt ttt aca gct gtg ggg cac ccg *gt ctt ggt tcc att
 M   X   *   F   X   G   Y   F   F   T   A   V   G   H   P   X   L   G   S   I
  X   F   N   F   X   A   T   F   L   Q   L   W   G   T   X   V   L   V   P   F
   X   L   I   X   R   L   L   F   Y   S   C   G   A   P   X   S   W   F   H   L
541/181
tgg aag t*g atg aaa *aa tgt ttt a
 W   K   X   M   K   X   C   F
  G   S   X   *   X   N   V   L
   E   X   D   E   X   M   F
```

FIG. 9

```
1/1                                        31/11
tgc ccc ctg gat ggc atg tgg tgc ttg gag ggt tgt ggt tgc aaa cgt gac agg CCG TAC
 C   P   L   D   G   M   W   C   L   E   G   C   G   C   K   R   D   R   P   Y
   A   P   W   H   A   C   G   A   W   R   V   V   V   A   N   V   T   G   R   T
     P   P   G   W   H   V   V   L   G   G   L   W   L   Q   T   *   Q   A   V   H
61/21                                      91/31
ATG CAC TGT CCA CGT AAG TTC CGC TTA CAA AAA ATT TGG TTG TAC AAG CAA TAC AGA GAG
 M   H   C   P   R   K   F   R   L   Q   K   I   W   L   Y   K   Q   Y   R   E
   C   T   V   H   V   S   S   A   Y   K   K   F   G   C   T   S   N   T   E   S
     A   L   S   T   *   V   P   L   T   K   N   L   V   V   Q   A   I   Q   R   V
121/41                                     151/51
TAA GAG TAC ACA TCT CGA TGA CTT ACC TGC TGT GAT TTA ATA TTT CAG ATA TAC CGA GAA
 *   E   Y   T   S   R   *   L   T   C   C   D   L   I   F   Q   I   Y   R   E
   K   S   T   H   L   D   D   L   P   A   V   I   *   Y   F   R   Y   T   E   K
     R   V   H   I   S   M   T   Y   L   L   *   F   N   I   S   D   I   P   R   S
181/61                                     211/71
GTT GAA ACT CCT GGA AGA AAC AGT TTA ATC TAC CAC TCA ATA ACC AAG AAG GGA CCT TTG
 V   E   T   P   G   R   N   S   L   I   Y   H   S   I   T   K   K   G   P   L
   L   K   L   L   E   E   T   V   *   S   T   T   Q   *   P   R   R   D   L   C
     *   N   S   W   K   K   Q   F   N   L   P   L   N   N   Q   E   G   T   F   A
241/81                                     271/91
CAT GAA ACC CCA ATC AGT GAT CAA TAT AAG CCC CTG GGA TAT CTC GAC AGG CAA CGT TTA
 H   E   T   P   I   S   D   Q   Y   K   P   L   G   Y   L   D   R   Q   R   L
   M   K   P   Q   S   V   I   N   I   S   P   W   D   I   S   T   G   N   V   *
     *   N   P   N   Q   *   S   I   *   A   P   G   I   S   R   Q   A   T   F   S
301/101                                    331/111
GCA GCA AGG AGG AGT AAC ACT ACT TAT TGC TAT GAC TTC CCG TTG GTT TGT TAC T
 A   A   R   R   S   N   T   T   Y   C   Y   D   F   P   L   V   C   Y
   Q   Q   G   G   V   T   L   L   I   A   M   T   S   R   W   F   V   T
     S   K   E   E   *   H   Y   L   L   L   *   L   P   V   G   L   L
```

FIG. 10

```
SCORES    Init1: 87  Initn: 139  Opt: 125
          38.4% identity in 73 aa overlap 10        20        30        40        50
Arab      RPYFLQAAVPLLYPCTRIMYCLFLFNFVEIRRFYGIEHGGGYDSWRKTSVVAF
                         ||::  :||::||:       ::|  ::
Rat       PRLQVEHPCTEMVADVNLPAAQLQIAMGIPLFRIKDIRMMYGV------SPWGDA-----
         440       450       460       470       480

60        70        80        90       100       110
Arab      PFDFDKAQSIR-PKGHCVAVRVTSEXPDDGFKPTSGRVQVMZYLWNAKZKFIHZGTLWGN
          |:||::::  ::  |:||  :|:|:|||:||:||||:||  ||   :::
Rat       PIDFENSAHVPCPRGHVIAARITSENPDEGFKPSSGTVQELNFRSNKNVWGYFSVAAAGG
         490       500       510       520       530       540

120       130       140       150       160       170
Arab      TCMNLQQXLSFKSKPNVWAYFSVKVIYIYXXSAIZVFHNXLIXRLLFYSCGAPXSWFHLE Rat       LHEFADSQFGHCFSWGENREEAISNMVVALKELSIRGDFRTTVEYLIKLLETESFQLNRI
         550       560       570       580       590       600
```

---

```
SCORES    Init1: 87  Initn: 116  Opt: 117
          46.5% identity in 43 aa overlap 30        40        50        60        70        80
Arab      LFNFVEIRRFYGIEHGGGYDSWRKTSVVAFPFDFDKAQSIR-PKGHCVAVRVTSEXPDDG
                    ::||::::  ::  |:||  :|:|:|||:||:|
Chick     AAQLQIAMGIPLHRIKDIRVMYGVSPWGDGSIDFENSAHVPCPRGHVIAARITSENPDEG
         460       470       480       490       500       510

90       100       110       120       130       140
Arab      FKPTSGRVQVMZYLWNAKZKFIHZGTLWGNTCMNLQQXLSFKSKPNVWAYFSVKVIYIYX
          |||:||  ||   :::
Chick     FKPSSGTVQELNFRSNKNVWGYFSVAAAGGLHEFADSQFGHCFSWGENREEAISNMVVAL
         520       530       540       550       560       570
```

FIG. 11C
REGION A

```
TCGACTCGATCTGAAAATATCTAGTGTTCAACAAACTTCAGATTCTTCGATCTACATATAAAT
CTGTTACATTCTTTTTATCAAAGAAATCACATTATTTAGTAACTAATCCTAACTATAAA
ATCTTTATTCAAGTATTGATTATCCTTGATGAACTTTTAACAAACGGAATCAAATATAGGAA
ACTAAATCGACCTATACAGAAAATAATATTTAAATACAATACTTTTTTCCTACTTAGCAC
TTGGATGGCTTTATGGCTTCATGATCTAGTGGAGCAAGATCAGTAGAGATTGATATGGTT
CAAGTTTGTTCTGGTCTAGTTTTTACGGGCATTTTATGTACCTCGTGAACTTTCAAGTTATA
AAATCCCGGTGCCCTTGGAAAAAAAGGTCTCAAGACATAAGCATACAATAAATTTGTTT
TACAAAGTTTGGAACAAGTCAAGATCAGTGATTCGTTAATTTTCATTGCTAAAATGATTGGATCA
TTCACAATTAACAAAAATGAGGAAAGAATGAGAGAAAGATAAGGTTGCCATACAATA
TAAACCCATACCTAACTCTCAACTATATCTCAACCCCAGTCATTTATAGTTACTATTAAGCC
ATTAATATATTATTTCTTTGTCAATGAGACCACTTTTATTCTCATTTTAAATAATCAAACAAAAT
GAAGAT
```

FIG. 11C
REGION Aii

```
GAACTACTATTATCTGAATTAACCGTGTTTACTGTACAGAACACATGTATTAAGCTCAATTT
CAGCAATGAAGTTTGGTCTTTGGAGTTATTGTGTCATTCATCTGAACATCTTTGTCTACAACC
TGTGTGCAGATGGCTGAAGTAACACGCCGTGGATGCCAGTTTGGCCTGGTTGGGGTCATGCAT
CTGAAAACCCGAATTACCTGATGCCCTAGATGCAAAAGGAATCATATGTCTTGGTCCTCCA
GCATCTTCAATGGCAGCACTGGGAGATAAGATTGGTTCTTGTTGATTGCACAAGCTGCTGA
TGTACCCACTCGCCATGGAGTGGTCCCATGTAAGTAAATTACTCTTGTTAAGCTTGAGTA
TTCTATAGTGTCACCTAAATA
```

FIG. 11C
REGION B

```
GGAGGGTCCAATTACTGTGCTCCGCCAGAAACTTTCAAGAAACTTGAACAAGCAGTAGA
AGGTTGGCTAAGAGTGTTAACTATGTTGGAGCTGCTACTGTTGAGTATCTCCACAGTATGGA
CACTGGGGAGTACTACTTCTTAGAGCTTAACCCTCGCTTACAGgtgtttcatactgagc
tttttgcgttgaaatataagaagtccgactgaaaattgaatgacttgtttaacttgat
gtttgagGTCAGGTTGAGCATCCTGTCACTGGATTGCCGAGATAAATCTTCCTTCTGCCCA
AGATATACTGTGGGGATGGGAATTCCTCTGGCAAATCCCTGGTATAATCTACGTCCTTAT
TTCTTACAGgcagcggttcctccttcattccatgcacacgaataatgtactgtctgtttct
cttaattttcgtagagataagacggttcatggaataagaaacatgtggagGTTATGATTCTT
GGCGAAAACATCTGTTGTAGCCTTCCCTTTGATTTTGATAAAGCTCAATCTATAAGGCCA
AAGGTCATTGTGTGGCTGTGCTGTGACAAGTGAGGATCCTGATGACGGGTTCAAACCAA
CCAGCGGTAGAGTTCAGgtaatgtgatatctgtggaatgcaaagtgaaagttcattcactg
agaacctgtgggtaacactgtatgaactgcaacagGAGTTGAGTTTTAAGAGCAAGCC
AAATGTGTGGGCGTACTTCTCTGTCAAGgtaattatatctatagagactctgctatataag
tgtttcacaatgtttaaattttacgactactttttacagtctgtggagGCATCCACGA
GTTCTCG
```

FIG. 11C
REGION C

```
ctatgtaagaacctcttttctcagagaATTTATTGTCTTGAAAAGTTTCTATCTGGTGACGA
AATGTTCTATCTGTCCAGAAGCATCAGGACCAGTGCTGTCGTGTTCAGATTACGTTGG
TTATCTCGGAGAAGGGCAAATCCCTCCAAAGgtaatcaataccaggatctctttgcct
tctagtgatgttcttgtagctaacttttctctcttaacttgcagcatatatctctgtaca
ttccaagtctctgaatattgaagGAAGTAAATATACGGTATTCGCCTACTATCCAAATT
TTACGTCTCTGCAATTTCGTATTTTCCCTCTGCCATATTATTTTGCGCTGAAGATATTGTTA
CCAGgctactaacatgaacataacgttctagagtgattagcaatgtagtccggtgat
cagGAACCTACAGGCTAAGAACAAGTGAACAAGTCAGAAGTGTAGCAGAAATACACACTCTACGT
GATGGAGGTCTGTTGATGCAGgcaagttttcgcctttctatactacaagacaagacat
acatgtgtcgcgcagaaaaaaacttctggagaatctcactcctttcttgtttcactgtc
attgcagttgatggcaaagccatgatatgcagagGAAGAAGCTGCAGGAACTCGTC
TTCTCATTGATGGAAGAACTGTTGCTACAGgttctgctaattttttgtgtgtttacca
tttacttcacgttctctgaagtcatcttaagctgtctgtcaattttggctta
ttcagAATGACCATGATCCATCAAAGTTAATGGCTGAGACACCGTGCAAGTTGATGAGGTAT
TTGGTTTCTGACAACAGCAATATTGACGCTGATACGCCTTATGCCGAAGTTGAGGTCATGAA
GATGTGCATGCCACTCTTTCACCGTCTCAGGAGTTATCCATCTTAAAATGTCTGAAGGAC
AAGACATGCAGgttcacttcattgctaacaaaagtcacagttcgttaattgattaa
ccatccattattttttcacagGCTGGTGAACTTATCGCCAATCTTGATCTTGATGATCCT
TCTGCTGTAAGAAAGGCCGAACCCTTCCATGGAAGTTTCCAAGATTAGGGCTTCCAACTGC
AATATCCGGTAGAGTTCATCAGAGATGTGCCGCAACATTAAATGCTGCACGCATGATTCTTG
CTGGCTATGAGCATAAAGTAGATGAGgtaaacacgttgttttccatttgatcaactc
tcctactcagattatttgactatgagatagctcatacgtcgcagGTTGTTCAAAGACTTACT
TAATTGCCTTGATAGCCCTGAACTCCCATTTCTTGCAGTGGCAACAGTGCTTTGCAGTTCTG
GCGACACGACTACCTAAAAATCTCAGgaacatgtaacacctgtagtattcataataatccg
gttctttatattgattttttggttcaagactttttaatcatatctaaataaactt
tatcagctagaatcaaagtatagGGAATTTGAGAGTATTTCCAGAAACTCTTTGACCACCG
ATTTCCCTGCCAAACTTTTAAAGGCAGTC
```

FIG. 11C
REGION D

```
CGAGTCAATTACTTGAACAGACCAAACTAAGTGAAGCTTCGTTCAAACATTGCTAGAAGCC
TTTCAGAGTTAGAAATGTTTACAGAGGAGCGGAGAAAATATGGATACTCCAAGAGGAAAA
GTGCCATTAATGAAAGAATAGAAGATCTTGTAAGCCGCATCTTTAGCTGTGTTGAAGCGTCT
CGTGGGACTATTTGACCATAGCGATCACACACTTCAAAGACGGGTTGTTGAGACTTATATT
CGCAGATTATACCAGgttcgagttcattcttccgcaccctattgttcaaaattcttttg
tactgcaattgattacagAAAATTTTGACTTCATTTTAACCGACTCTGTCATCAGCCCT
ACGTCGTTAAAGATAGCGTGAGgatgcagtcgcgccgatgcagtgcacctttctggtct
tcttgattcctagagGAGCATATGGAAAGAAGAAAACATTGGTTTAGACGAT
CACGACACATCTGAAAAAGGATTGGTTGAGAAGCGTAGTAAGAGAAAATGGGGGCTATG
GTTATAATCAAATCTTTGGAGTTTCTTCCACGTATAATACGTGCAGCATTGAGAGAAACAT
AGCACAACGACTATGAAACTGCCGGAGCTCCTTTATCTGGCAATATGATGCACATTGCTAT
TGTCGGGCATCAACAACCAGATGAGTCTGCTTCAGGACCAGGTACTTGACACAGTAT
```

FIG. 11C
REGION E

```
ACCGAGAAGTGAACCTGAAGAAACAGTTAATTCTACCACTCAATAACCCAAGAAGGGACCT
TTGCATGAAACCCAATCAGTGATCAATATAAGCCCCTGGGATATCTCGACAGGCAACGTT
TAGCAGCAAGGAGGAGTAACACTACTTATTGTCTATGACTTCCCGTTGgtttgttactgaat
tcataagattcacacataegcttactctttggctattcaaccccccttatgtattc
tttctttcagGCATTTGGGACAGCCTTGGAACTGTTGTGGGCATCACACACCCAGGAG
TTAAGAAACCATATAAGGATACTCTGATCAATGTTAAAGAGCTTGTATTCTCAAACCAGA
AGGTTCTTCTCCGACATCTCTAGATCTCGGTTGAAAGACACCACCGGTCTCAAGCACTTTGGA
ATGGTTGCCTGGTGCCTAGATATGTCGACCCAGAGTTCCTATGGGCGGAAACTTCTCG
TGATTGCGAATGATGTCACCTTCAAAGTCTTCTTTGGTCTTGATTTACTTGGCAGCAAAT
CCTTGCTGTTACTGAACTGCTTGGGGTTGCTGAAGAAGTCAAGCCTGCTTCAAGTTGGATGGTCGG
TCTGGTGCCCGACTTGGGTTGCTGAAGAAGTCAAGCCTGCTTCAAGTTGGATGGTCGG
ATGAAATTCCCGAGAATGGTTTTCAGTATATATAAGCCCTGAAGACCACGAAA
GGATTGGTCATCTGTCATTTGCCCATGAAGGTAAAGCTCCCTAGTGGGGAAACTAGGGTG
GGGTGAATTGATACGGTCGTTGGGCAAGAAGGATGG
```

FIG. 11C
REGION F gcaagctcgaattaaccctcactaaagGGAACAAAAGCTGGAGCTCTCTTGTAAAAACG
TAAGAGAAGCATCTGGAGACAACTTAGACATATAAATCTTCAATGCGTCTGATTCAGGATTG
GTTCTGCAACTCTGATATTGCAAAGGGAAAGAAGCTTGGACAGACGACCAAGTGTTC
TTTACATGGAAGGACACAATGTTAGTAACTACGAGTTGAAGCTGAAGCGAGTTGAGAGGCAGA
AACTACTGAACCAACTTGCAGAGATTGGGAATTCCTCAGATTTGCAAGCTCTGCCACAAGG
ACTTGCTAATCTTCTAAACAGggtataaacaaaccccccaaaaaacaagtttttggatgcaG
cccaagtaatcctaacctgtatgccggttttaaagcctaagtaatattttgatgcaG
GTGGACCGTCGAAAAGAAGAGAAGAGCTGGTGGGCTGCTATTCGAAAGGTCTTGGGTTGACTGA
TATCGAAGACTTTAGCTTCTAATCCAAGAAAGATGGACATTTAAGTTTGCTGTGTCCAT
TTGGACCATCTCCTTATATTTGTTGGTCACAGTTGTAAATGTTGTTGTAGCTTTGTCATT
TCCGTATAAACAATTACGCAATAATTCATTCAACACATGTCACTCTGCTTCATATTTATAC
ACTGAACCAAGACACAATATATAGTCTAAATATAAAACTGATCGGTCGACGCCCTATAGTGA
GTCGTATTAAGCCGGGCCGAGCTCTAGAGTC

FIG. 12A

```
      |       10         20         30         40         50         60         70         80
    1 AGRRLAKSVN YVGAATVEYL YSMDTGEYYF LELNPRLQVE HPVTEMIAEI NLPAAQVAVG MGIPLWQIPE IRRFYGIEHG
   81 GGYDSWRKTS VLASPFDFDK AESIRPKGHC VAVRVTSEDP DDGFKPTSGK VQELSFKSKP NVWAYFSVKS GGGIHEFSDS
  161 QFGHVFAFGE SRALAIANWV LGLKKNQNRG KIRTNVDYTI DLLHASDYRE NQIHTGMLDS RIAMRVRAER PPWYLSVVGG
  241 ALYKASATSA AVVSDYVGYL EKGQIPPKHI SLVHSQVSLN IEGSKYTIDV VRGGSGSYRL RMNNSEVVAE IHTLRDGGLL
  321 MQLDGKSHVI YAEEEAAGTR LLIDGRTCLL QNDHDPSKLM AETPCKLLRY LVSDNSSIDA DMPYAEVEVM KMCMPLLSPA
  401 SGVIHFKMSE GQAMQAGELI AKLDLDDPSA VRKAEPFHGG FPRLGLPTAI SGKVHQRCAA TLNAARMVLA GYEHKVDEVV
  481 QDLLNCLDSP ELPFLQWQEC FAVLATRLPK DLRMMLESKY REFESISRNS LTADFPAKLL KGILEAHLLS CDEKDRGALE
  561 RLIEPLMSLA KSYEGGRESH ARVIVHSLFE EYLSVEELFN DNMLADVIER MRQQYKKDLL KIVDIVLSHQ GIKDKNKLVL
  641 RLMEQLVYPN PAAYRDKLIR FSTLNHTNYS ELALKASQLL EQTKLSELPA SNIARSLSEL EMFTEDGENM DTPKRKSAIN
  721 ERMEDLVSAS LAVEDALVGL FDHSDHTLQR RVVETYIRRL YQPYVVKESI RMQMHRSGLI ASWEFLEEHI FRKHML  796
``` ii  Yeast Biotin binding site AA 727    PYAE | I | EVMKM | Q | MPL | V | S

Rape derived AA 384    PYAE | V | EVMKM | C | MPL | L | S

FIG. 12C

```
TGGCTGGTAGAAGGTTGGCTAAGAGTGTTAACTATGTTGGAGCAGCTACTGTTGAATATCTC
TACAGCATGGACACGGGGAGTACTACTTCTTAGAGCTTAACCCTCGGTTACAGGTTGAGC
ACCCTGTAACTGAATGGATTGCCGAGATAAATCTTCCTGCTGCGCAAGTTGCTGTTGGGATG
GGAATTCCTCTCTGGCAAATCCCTGAGATAAGACGGTTCTATGGTATAGAACATGGTGGAGG
TTACGATTCTTGGAGGAAAACATCTGTGCTAGCCTCCCCTTTTGATTTTGATAAAGCTGAATC
TATAAGGCCAAAAGGTCATTGTGTGGCTGTACGCGTGACAAGTGAGGACCCTGATGACGGA
TTCAAACCCACCAGCGGTAAAGTACAGGAGTTGAGTTTTAAAAGCAAGCCAAATGTGTGGG
CTTACTTCTCTGTCAAGTCTGGTGGAGGCATCCACGAGTTCTCAGATTCCCAATTTGGCCATG
TTTTTGCATTTGGGGAATCCAGAGCCTTGGCAATAGCAAATATGGTCCTTGGGCTTAAAAAA
AATCAAAATCGTGGAAAATTAGGACTAACGTTGACTACACGATTGACCTTTTACATGCTTC
TGATTACCGGGAAAACCAAATTCACACTGGTTGGTTGGACAGTAGAATTGCTATGCGGGTC
AGGGCAGAGAGGCCTCCATGGTACCTCTCTGTTGTCGGAGGGGCTCTCTATAAAGCATCAG
CGACCAGTGCTGCTGTAGTCTCGGATTATGTTGGTTATCTAGAGAAGGGACAAATTCCCCC
AAAGCATATATCTCTTGTGCATTCTCAAGTGTCTCTGAACATTGAAGGAAGTAAATATACGA
TTGATGTGGTCCGGGGTGGATCAGGAAGCTACAGGCTAAGAATGAACAACTCAGAAGTTGT
AGCAGAAATACACACTCTACGTGATGGAGGTCTGTTGATGCAGTTGGATGGTAAAAGCCAT
GTGATATATGCAGAGGAAGAAGCTGCAGGAACCCGTCTTCTTATTGACGGAAGAACTTGTT
TACTTCAGAATGATCACGATCCTTCAAAGTTGATGGCTGAGACACCGTGCAAGCTGCTGAG
GTATTTGGTTTCAGATAATAGCAGTATTGATGCTGACATGCCCTACGCGGAAGTTGAGGTCA
TGAAGATGTGCATGCCACTTCTTTCACCTGCATCAGGAGTTATACATTTCAAAATGTCTGAA
GGACAAGCCATGCAGGCTGGTGAACTTATAGCCAAGCTTGATCTTGATGATCCTTCTGCTGT
AAGAAAGGCCGAACCCTTCCATGGAGGTTTCCCAAGATTAGGGCTTCCAACGGCAATTTCTG
GTAAAGTTCATCAGAGATGTGCTGCAACTTTAAATGCTGCTCGCATGGTTCTTGCCGGCTAT
GAGCATAAAGTAGATGAGGTTGTTCAAGACTTGCTTAACTGCCTTGATAGCCCTGAACTCCC
ATTCCTTCAGTGGCAAGAGTGCTTCGCAGTTCTGGCAACACGACTACCGAAAGATCTCAGAA
TGATGTTAGAATCCAAGTATAGGGAATTTGAGAGTATATCCAGGAACTCTCTCACCGCAGAT
TTCCCTGCCAAACTTTTAAAAGGCATTCTTGAGGCTCATTTATTATCTTGTGATGAGAAAGAT
AGGGGTGCCCTTGAAAGGCTCATTGAACCATTGATGAGCCTTGCAAAGTCTTATGAAGGTG
GTAGAGAAAGTCATGCCCGTGTTATTGTTCATTCTCTTTTTGAAGAATACCTATCTGTAGAA
GAATTATTCAATGATAACATGCTGGCTGATGTTATTGAACGCATGCGTCAGCAATACAAGAA
AGATCTGTTGAAGATTGTTGATATTGTGCTCTCACACCAGGGCATTAAAGACAAAAACAAAC
TCGTTCTTCGGCTCATGGAGCAGCTTGTTTACCCTAATCCTGCTGCATACAGAGATAAACTTA
TCCGATTCTCGACACTAAACCATACTAATTACTCTGAGTTGGCACTGAAGGCAAGCCAATTA
CTCGAACAGACCAAATTAAGTGAACTTCCAGCTTCAAACATTGCTAGAAGCCTGTCAGAGTT
AGAAATGTTTACAGAGGATGGGGAAAATATGGATACTCCCAAGAGGAAGAGTGCCATTAA
TGAAAGAATGGAAGATCTTGTGAGCGCATCCTTAGCTGTTGAAGATGCTCTCGTGGGACTA
TTTGACCACAGCGATCACACACTTCAAAGACGAGTTGTTGAGACTTATATTCGCAGATTATA
TCAGCCCTACGTCGTCAAAGAAAGCATCAGGATGCAATGGCACCGGTCTGGTCTTATTGCTT
CTTGGGAGTTCCTAGAGGAGCATATTTTCCGGAAACATTGGCTTA
```

PLANT GENE SPECIFYING ACETYL COENZYME A CARBOXYLASE AND TRANSFORMED PLANTS CONTAINING SAME

This invention relates to a plant gene specifying the enzyme acetyl Coenzyme A carboxylase (ACCase) and to plant genomes genetically transformed with the said gene. Particularly, but not exclusively, the invention relates to ACCase genes from plants of the Brassica species, especially *Brassica napus* (oilseed rape) and control of expression of the gene by Brassica plants which are genetically transformed with the gene or its antisense configuration.

Acetyl Coenzyme A carboxylase is one of the genes involved in the synthesis of oil by oil-producing crops such as oilseed rape. Variation of the expression of that gene leads to alteration in the quantity and/or quality of the oil produced.

An object of the invention is to provide a gene specifying ACCase in plants.

According to the present invention there are provided partial cDNAs specifying ACCase, isolated from seed of *Brassica napus*, having the nucleotide sequences set forth in FIGS. 6 and 12, and variations thereof permitted by the degeneracy of the genetic code.

The invention further provides the partial cDNA, isolated from wheat germ, having the nucleotide sequence set forth in FIG. 4, and variants thereof permitted by the degeneracy of the genetic code.

Also provided by this invention is the full length genomic DNA specifying ACCase from *Arabidopsis thaliana* having the nucleotide sequence set forth in FIG. 8, and variants thereof permitted by the degeneracy of the genetic code.

The invention further provides the following clones, inserted in *Escherichia coli*, strain DHα hosts, which have been deposited with the National Collection of Industrial & Marine Bacteria, 23 St. Machar Road, Aberdeen, AB2 1RY, United Kingdom, on Mar. 25, 1993, under the provisions of the Budapest Treaty on the Deposit of Microorganisms for Patent Purposes, details of which are as follows:

1. Plasmid pK111, Accession No. NCIB 40553
2. Plasmid pKLU81, Accession No.NCIB 40554
3. Plasmid pRS1, Accession No. NCIB 40555

The present invention also provides genetically transformed plants, plant cells and plant parts, containing a DNA of the invention or fragment thereof in sense orientation or a complete or partial sense or antisense variant thereof.

It is preferred that the plant be of a species which produces substantial quantities of oil, rather than starch. Such plant species are well known and are simply referred to as "oil-seed" crops and include, oilseed rape, canola, soya and sunflower. Methods for the genetic transformation of many oil crops are known; for example, transformation by *Agrobacterium tumefaciens* methods are suitable for most. Such methods are well-described in the literature and well-known and extensively practised in the art.

In our International Patent Application Number WO 92/19747, published on Nov. 12, 1992, we describe the biosynthesis of polyhydroxybutyrate from the substrate, acetyl-CoA. This activity involves three enzyme-catalysed steps. The three enzymes involved are β-ketothiolase, NADP linked acetoacetyl-CoA reductase, and polyhydroxybutyrate synthase, the genes for which have been cloned from *Alcaligenes eutrophus* (Schubert et al, 1988, J Bacteriol, 170). In our international application we describe the cloning of these three gene into oil-synthesising plants.

However, the synthesis of fatty acids which are the building blocks of plant oils utilise the substrate acetyl Coenzyme A which is the same substrate required by the polyhydroxyalkanoate genes. By virtue of the present invention we provide means for down-regulating the fatty acid synthesis by inhibiting ACCase thereby leaving the acetyl CoA available for conversion to polyhydroxyalkanoates.

Methods for the regulation of gene expression are well-known in the art. Two principal methods are commonly employed, these being referred to loosely as "sense" and "antisense" regulation. In antisense regulation a gene construct is assembled which, when inserted into a plant cell, results in expression of a messenger RNA which is of complementary sequence to the messenger produced by a target gene. The theory is that the complementary RNA sequences form a duplex thereby inhibiting translation to protein. The complementary sequence may be equivalent in length to the whole sequence of the target gene but a fragment is usually sufficient and is more convenient to handle. In sense regulation a copy of the target gene is inserted into the plant genome. Again this may be a full length or partial sequence. A range of phenotypes is obtained from which individuals in which the expression of the protein encoded by the target gene is inhibited may be identified and isolated as may individuals where expression of the gene product is increased. Sense regulation using partial sequences tends to favour inhibition. The mechanism is not well understood. Reference is made to European Patent Application No. 140,308 and U.S. Pat. No. 5,107,065 which are both concerned with antisense regulation and International Patent Application No. WO 90/12084 which describes sense regulation. The invention permits the following genetic modifications to be effected:

1. The clones of the invention may be used to probe plant DNA (genomic or cDNA libraries) to obtain homologous sequences. These may be truncated or full length cDNAs or genomic DNAs for ACCase genes from, for example, wheat, or oil crops such as rape, canola, soya, sunflower, maize, oil palm and coconut.

2. Partial cDNAs of rape seed ACCase may be used in conjunction with a plant-recognised promoter to create an expression cassette (partial sense or antisense) for use in transforming rape plants to down-regulate production of the ACCase enzyme. This will give plants with a lower oil content or oil of altered quality. The same cassette can be used to down-regulate the production of ACCase enzyme in other plants of the Brassica species. cDNAs isolated from other crops can be used to create expression cassettes (partial, sense or antisense) for use in transformation of these crops in order to modify the oil content.

Down-regulation of oil synthesis (in rape or other oil crops) can be used to divert the substrate, acetyl Coenzyme A, into synthesis of alternative storage materials such as starch, protein, or novel polymers introduced by genetic modification, for example polyhydroxyalkanoates.

3. Full length clones of rape or Arabidopsis ACCase DNA can be used to create expression cassettes, either with powerful promoters, or by inserting extra gene copies, to promote over-expression of ACCase in rape or other oil crops, leading to plants with enhanced oil content in the seed. The ACCase DNA may also be put under the control of a seed-specific promoter such as the napin promoter, which has a different window of expression from the ACCase promoter during seed development. In this way the period over which ACCase is expressed in the developing seed is extended, and the oil content of the seeds increased.

4. Genomic DNAs of rape ACCase can be used to recover the promoter of the ACCase gene. This promoter can be used to generate RNA in a tissue-specific and developmentally regulated fashion. The promoter so generated may promote the expression of ACCase, or it may control the expression of a gene construct placed after it (for example the structural gene of a different enzyme) which will then be expressed specifically in the developing seed.

5. The full length cDNA and genomic DNA of rape or Arabidopsis ACCase contain a sequence between the translation start site and the N-terminal sequence of the mature protein, known as a "transit peptide" sequence. This directs the gene product to the plastids and is cleaved off during import of the protein into the plastids. This transit peptide sequence may be used in gene fusions to direct different gene products to the plastids.

6. Monocotyledonous plants, such as wheat, barley, maize and rice, are normally sensitive to the aryloxyphenoxypropionate and alkylketone herbicides to which the dicotyledonous plants are normally resistant. Monocots with resistance to these herbicides may be created by:

(a) transforming ACCase from a dicotyledonous species such as rape and Arabidopsis, into the monocot genome;

(b) overexpression of the ACCase in a monocot; or, (c) mutagenesis of ACCase and insertion of the mutant gene into a monocot.

7. It is believed that ACCase activity exists in both the plastid and the cytosol. Partial cDNAs of rape seed ACCase of this invention may be used in conjunctipon with a plant-recognised promoter to create an expression cassette (partial sense or antisense) for use in transforming plants to down-regulate production of the cytosolic ACCase. This will alter oil quality by inhibiting production of long chain fatty acids) chain length greater than about C18).

8. A second plastid form of ACCase has been identified in plants. This ACCase is composed of dissociable sub-units for transcarboxylase, biotin carrier protein (BCP) and biotin carboxylase (BC). The transcarboxylase gene is encoded by the chloroplast genome; BCP and BC are nuclear encoded. Sequence homology between the cDNAs of the invention and the BCP and BC may be used to isolate BCP and BC. Sense and antisense constructs may be raised against BCP and BC in order to effect down-regulation of these genes.

9. The cDNAs of the invention may themselves have sufficient homology with the BCP and BC genes to be used directly for the down-regulation of these genes.

We have prepared a poly dT primed cDNA library from developing rape seed and have obtained another from developing wheat embryo. These libraries have been probed with DNA fragments isolated earlier from a partial length maize leaf ACCase DNA (pA3) and partial length cDNA clones specifying rape seed ACCase (pRS1) and wheat germ ACCase (pK111) have thereby been selected and sequenced.

A DNA fragment isolated from the partial length rape ACCase DNA was then used to probe a genomic DNA library prepared from *Arabidopsis thaliana* and a full length Arabidopsis genomic DNA selected and sequenced.

The sequence of the Arabidopsis genomic DNA was used to generate specific probes by PCR. These were used to screen a random primed cDNA library from rape seed and two further rape ACCase partial cDNAs were thus isolated.

The full length Arabidopsis ACCase genomic DNA may then be used to probe a genomic library from rape and the full length rape ACCase genomic DNA selected and sequenced.

That the clones were indeed of ACCase genes was confirmed as follows:

The deduced amino acid sequence for wheat ACCase cDNA shows complete homology in four regions of sequence to the amino acid sequences obtained from four peptides isolated from the ACCase enzyme purified from wheat embryo. The deduced amino acid sequence shows high homology with both the rat and chicken ACCase genes. High homology at the amino acid level with maize leaf ACCase was found, with two sections of 48 amino acids completely conserved.

The deduced amino acid sequence from the rape seed partial cDNA (pRS1) sequence shows high homology to the sequences of the maize leaf cDNA and the chicken, rat, yeast and algal ACCase genes.

The deduced amino acid sequence from the Arabidopsis genomic DNA shows high homology with the rat, chicken and yeats ACCase genes. High homology with the amino acid sequence of the rape seed ACCase partial cDNA (pRS1) was found, with one section of 48 amino acids almost completely conserved.

BRIEF DESCRIPTION OF THE DRAWINGS

The invention will now be described with reference to the accompanying drawings which show:

FIG. 3 shows a comparison of four sections of amino acid sequence deduced from the pK111 wheat ACCase cDNA with the amino acid sequences obtained from four peptides isolated from the purified wheat embryo ACCase enzyme (SEQ ID NOS:1–8;

FIG. 4 shows the sequence of the sense strand of the wheat embryo ACCase clone pK111 (SEQ ID NO:9), with three-phase translation shown (SEQ ID NO:10). The sequences homologous with the peptide amino acid sequences are underlined;

FIG. 6a shows the derived amino acid sequence (SEQ ID NO:11) from the rape cDNA encoding the transcarboxylase domain of ACCase. The amino acid sequence is translated from the first open reading frame shown pictorially. The full vertical lines represent stop codons and the half vertical lines ATG sequences.

FIG. 6b shows the nucleotide sequence (SEQ ID NO:12) of the cDNA clone pRS1, corresponding to the trans carboxylan domain of ACCase.

FIG. 7 shows the rape transcarboxylase domain comparison with known ACCase sequences. The Dot Matrix (DNA Strider, Stringency 9 Window 21) of derived rape ACCase amino acid sequence (transcarboxylase domain) is compared against rat, yeast and algal (Chlorella) ACCase.

FIG. 8 shows the 5' sequence (SEQ ID NO:13) from the sense strand of the Arabidopsis genomic subclone pKLU81, with three phase translation shown (SEQ ID NO:14).

FIG. 9 shows the 3' sequence (SEQ ID NO:15) from the sense strand of the Arabidopsis genomic subclone pKLU81, with three-phase translation shown (SEQ ID NO:16).

FIG. 10 shows a comparison of the Arabidopsis pKLU81 5' translated open reading frame (SEQ ID NO:17) with the sequences of rat and chicken ACCase genes (SEQ ID NOS:18 –19) obtained from SWISSPROT database.

FIG. 11 shows the assignment of domain order to higher plant ACCase.

In FIG. 11Bii) the translated open reading frame (SEQ ID NO:22) corresponding to the biotin binding site in area C is shown in direct comparison with the biotin binding site of yeast (SEQ ID NO:23). Boxed regions represent amino acid identity.

FIG. 11Biii) shows a DNA sequence comparison by dot matrix (DNA Strider, Stringency 15 Window 23) of the rape transcarboxylase domain of ACCase and areas E/F from the Arabidopsis genomic clone.

FIG. 11C shows the nucleotide sequences (SEQ ID NOS:24–30) of Regions A, Aii, B, C, D, E, F, Arabidopsis genomic clone pKLS2.

FIG. 12 shows the rape ACCase biotin binding domain sequence.

FIG. 12Ai) shows the derived amino acid sequence (SEQ ID NO:31) from the rape cDNA encoding the ACCase biotin binding domain. The actual biotin binding site is shown underlined.

FIG. 12Aii) shows the direct comparison of the biotin binding site with that of the corresponding sequence of yeast ACCase. The boxed regions represent amino acid sequence identity.

FIG. 12C shows the full combined nucleotide sequence (SEQ ID NO:32) of pRS6 and pRS8.

FIG. 14 shows Northern blot analysis of rape ACCase.

Figure 1A:
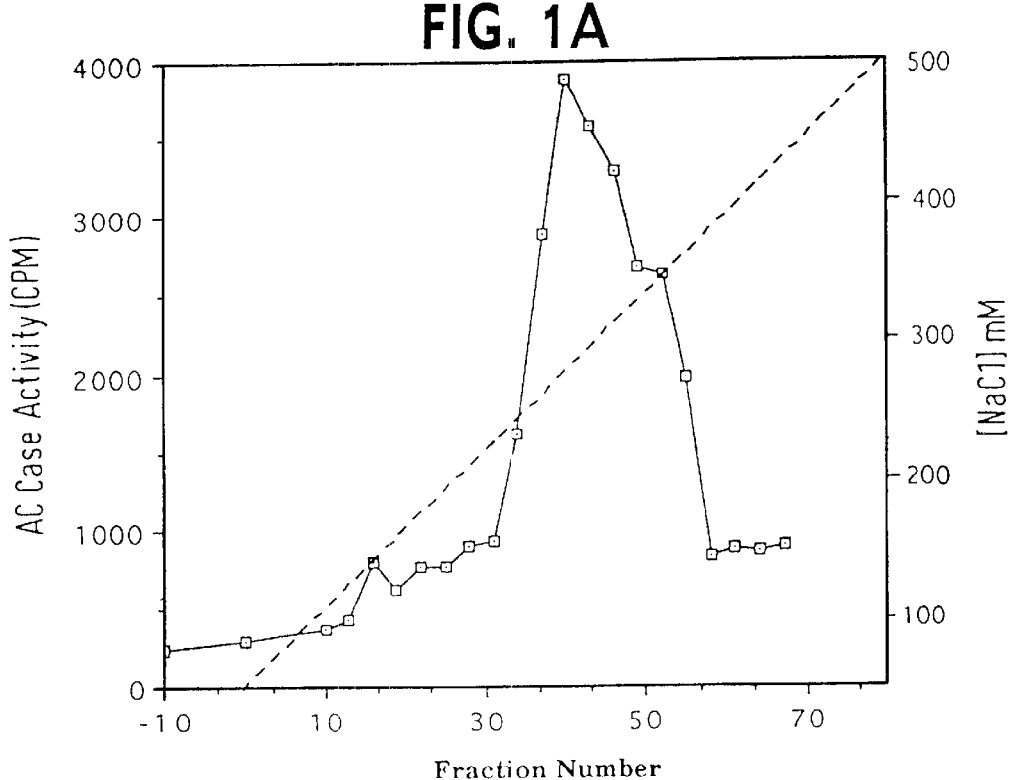
FIG. 1 shows the elution profiles of wheat embryo ACCase from Q-Sepharose (FIG. 1A) and Blue-Sepharose (FIG. 1B) during purification of the enzyme. The dotted line represents the sodium chloride gradient concentration and the activity of ACCase, represented by the boxes, was measured as described hereinbelow.

MATERIALS AND METHODS 1.0 Protein Purification and Amino Acid Sequence Data 1.1 Assay for ACCase Acetyl CoA Carboxylase activity was assayed by incorporation of radioactivity from $^{14}C$-bicarbonate into non-volatile malonyl CoA (Hellyer et al 1986).

1.2 SDS Poly-Acrylamide Gel Electrophoresis

All SDS PAGE gels consisted of a 3% stacking gel with a 7.5% running gel on a mini Biorad Protean gel kit unless otherwise stated. The buffer system used was that of Laemmli et al (1970) unless otherwise stated. All gels used in separating peptides for sequencing were pre-run in the presence of 200 µM thioglycolic acid in the running buffer.

2.0 Cloning for Wheat/Rape/Arabidopsis ACCase 2.1 Preparation of competent XL1-Blue and KW251

*Escherichia coli* cells XL1-Blue and KW251 cells were grown overnight in 50 ml LB media/0.2% Maltose/50 µ/ml Tetracycline/10 mM $MgSO_4$. The cells were spun down at 3000 g for 10 mins and the cell pellet taken up in 2.5 ml 10 mM $MgSO_4$ and stored at 4° C. Cells were used fresh for primary screening and no older than one week for subsequent screening.

2.2 cDNA Libraries 2.2.1 Wheat

The cDNA library used (gift of Dr Charles Ainsworth, Wye College, London) was generated using the pooled RNA from whole developing grain of Chinese Spring harvested at 3,5,7,10,15,25,30 and 35 days post anthesis. The cDNA was cloned into the EcoRI/XhoI site of λ-ZAP II (Stratagene) and the host bacteria used was XL-1Blue (see 2.1 for preparations of cells).

2.2.2 Rape (i) cDNA Library from PolyA+RNA

The cDNA library used was generated using the mRNA isolated according to the method of Logemann et al (1987) from mid stage developing *Jet neuf* rape embryos (harvested at approximately 35 days days post anthesis). The 1st strand synthesis was carried out using poly dT primers according to the manufacturers instructions (Amersham International). The resulting cDNA generated was cloned into the EcoRI/XhoI site of λ-ZAPII as recommended by the manufacturers (Strater gene). The host bacteria used was XL-1Blue (see 2.1 for preparation of cells).

ii) Random Primed Library

5 µg of poly A+mRNA from 35 day old (Post anthesis) *Jet neuf* rape embryo was used for the construction of a random primed cDNA library. The double stranded cDNA was prepared using a 1 in 10 dilution of pd(N)6 primers (0.74 µg/ul) according to the instructions provided with Time Saver™ cDNA synthesis kit (Pharmacia). The library was prepared in λZapII and packaged with Gigapack II Gold packaging extract (Stratagene). The host *E.coli* strain used was XL-1 Blue (Stratagene).

2.3 Genomic Libraries

The *Arabidopsis thaliana* library used (a gift from Dr John Cowl, John Innes Institute, Norwich) was derived from leaf total DNA in λ FIX II and the host bacteria used was *E.coli* KW251 (see 2.1 for preparation of cells).

2.4 Probe Preparation and Labelling

Plasmid DNA from pA3/DH5α (ICI derived) and pRS1/DH5α (see results for a description of pRS1) was prepared by the Quagen tip method. Probe for the screening of Wheat and Rape cDNA libraries was generated by the digestion of 10 μg pA3 with 20 U EcoRI or Hind III (New England Biolabs). The fragment isolated from the probe was 2.7 and 1.54 kb in length respectively. Probe for the screening of the Arabidopsis genomic library was generated by a Xho I/Pst I (10 U of each) double digest of 10 μg pRS1 to give an isolated fragment size of 1.2 kb. All digests were carried out in Pharmacia's "one-Phor-All Buffer PLUS" at 37° C. for 3 hours. Digests were separated by 1% TAE buffered agarose gel electrophoresis and the required fragments cut out from the gel. The DNA was obtained from the gel slice using the method recommended by Geneclean II (Bio 101). DNA concentration was determined by spectrophotometry.

The probes (200–300 ng) were radio-labelled with $p^{32}\alpha dCTP$ using the Megaprime kit as recommended by the manufacturers (Amersham International) to a level of $5\times10^9$ dpm/μg. Un-incorporated label was removed using Biospin chromatography columns (Biorad).

Just before use for hybridisation the radio-labelled probe was boiled for 5 minutes and placed on iced water for 2 minutes before being added to hybridisation buffer at 65° C.

2.5 cDNA Library Primary Screening

For the Wheat cDNA library 300,000 pfu's and the rape random primed and poly dT primed cDNA library 150,000 pfu's were added to 2 ml of competent XL1-Blue cells (150,000 pfu's/2 ml) mixed and incubated at 37° C. for 20 minutes. The culture was then added to 30 ml top agarose (150,000 pfu's/30 ml) which had been melted and held at 50° C., mixed briefly and poured onto pre-warmed (37° C.) large LB plates (243×243×18 mm). Plates were left at room temperature for 10 minutes and incubated overnight at 37° C. The plates were finally incubated at 4° C. for 30 minutes.

Square sheets of nitrocellulose were carefully placed onto the surface of each plate and allowed to soak in for 30 seconds, pealed off and placed onto 3 mm blotting paper soaked in denaturing buffer (1.5 M NaCl, 0.5 M NaOH) for 2 minutes. To neutralise the filters each was subsequently placed for 5 minutes onto 3 mm paper soaked in neutralising buffer (1.5 M NaCl, 0.5 M Tris pH 7.4) and finally for 5 minutes on 3 mm paper soaked in ×2 SSC. A second lift of 2 minutes was also carried out and treated in the same way. To immobilise the blotted DNA each filter was placed in a vacuum oven for 30 minutes.

The filters were incubated in pre-hybridisation buffer (50 mls ×6 SSC, ×1 Dendhart's, 0.5% SDS, 0.05% sodium pyrophosphate, 50 μg/$m^1$ herring sperm DNA with constant mixing for 3 hours at 65° C. at which point the buffer was discarded. The radio-labelled probe (see 2.4) was added to 10 ml hybridisation buffer (50 mls ×6 SSC, ×1 Dendhart's, 0.5% SDS, 0.05% Sodium Pyrophosphate, 1 mM EDTA) previously equilibrated to 65° C. The filters were incubated with constant mixing for 14 hours at 65° C. and the hybridisation buffer/probe removed but retained at −20° C. for the subsequent screens.

To wash off the un-bound probe the filters were washed 4 times with ×1 SSC, 0.1% SDS for 30 minutes at 65° C. Filters were air dried and exposed to film overnight. Positive plaques were located and pulled out from the plate using the wide end of a 1 ml gilson tip. Only plaques that showed up positive on both lifts (30 seconds and 2 minute lifts) were used. The plug was placed into 500 μl SM buffer with 10 μl chloroform and incubated at room temperature for 2 hours with occasional mixing. The suspension was spun for 5 minutes on a bench top centrifuge and the supernatant containing the pfu's retained.

2.6 Genomic Library Primary Screening

The methods used were as already described (see 2.5) but in a genetic manipulation isolation unit $2\times10^4$ were screened in total on 2 plates.

2.7 cDNA and Genomic Secondary Screening

50–200 pfu's in 200 μl SM buffer were added to 200 μl of competent XL1-Blue cells mixed and incubated at 37° C. for 20 minutes. The culture was then added to 3 ml melted top agarose at 50° C., mixed briefly and poured onto pre-warmed 37° C.) small LB plates (850 mm diameter). Plates were held at room temperature for 10 minutes and incubated overnight at 37° C. The plates were finally incubated at 4° C. for 30 minutes.

Pre-hybridisation and hybridisation was carried out in the same way as that in the primary screen (see 2.5), using the same probe/hybridisation buffer boiled for 5 minutes before use.

The procedure for lifting, preparing, probing, washing and exposing the nitro-cellulose filters was essentially the same as that already described (see 2.5).

The positive plaques were removed as a plug using the wide end of a 200 μl Gilson tip, placed into 500 μl SM buffer with 10 μl chloroform and incubated at room temperature for 2 hours with occasional mixing. The suspension was spun for 5 minutes on a bench top centrifuge and the supernatant containing the pfu's retained.

2.8 cDNA and Genomic Tertiary Screening

The method was essentially the same as that for the secondary screen (see 2.7) using only 10–20 pfu's per plant. Exposure of the nitrocellulose filters was only required for 2 hours in this instance.

2.9 Isolation of DNA from Positive Plaques

Plasmid rescue for cDNA clones was carried out as described by the Stratagene protocol for "in vivo excision of pSK from λ-ZAPII clones". The DNA from the pSK derived clones was prepared in large quantities using the Quagen tip method.

2.10 Preparation of Genomic DNA from Positive Plaques

One positive plaque was removed from a plate of the positive pfu's from the tertiary screen and incubated with 500 μl fresh KW 251 cells (see 2.1 for method of cell preparation) at 37° C. for 20 minutes. Pre-warmed LB media (50 ml at 37° C.) was added in addition to 500 μl M $MgSO_4$ and incubated with mild shaking at 37° C. for 5–7 hours. Following the 5–7 hours, 250 μl Chloroform was added to the culture and incubated for a further 15 minutes at 37° C. Cell debris was spun out at 10,000 g and DNase/RNase added to the supernatant to a final concentration of 1 μg $ml^{-1}$ and further incubation at 37° C. for 30 minutes. 5 g Polyethylene Glycol 8000/3.2 g NaCl was added slowly to the supernatant at 4° C. overnight with constant stirring.

The resultant suspension was pelleted at 10,000 g (4° C.) and taken up in 5 ml 20 mM Tris-HCl pH 7.4/100 mM NaCl/10 mM $MgSO_4$. The solution was then subjected to 3–5 chloroform extraction's and 3–5 1:1 Phenol:Chloroform extraction. To precipitate the DNA an equal volume of isopropanol (−20° C.) was added and left on ice for 30 minutes. The precipitated DNA was pelleted at 10,000 g and washed in 70% Ethanol (−20° C.) before being pelleted again. The DNA was resuspended in 300 μl $T_{10}E_1$ buffer.

Subcloning was carried out according to the method used by Sambrook et al (1989).

2.11 Sequencing of DNA Clones

Sequencing was carried out by the manufacturer's recommended methods for the machine used (Applied Biosystems Inc 373A DNA sequencer). Both forward and reverse primers (−21 m13 and M13RP1) were used initially for all clones. Oligonucleotides (20 mers) were generated and used to further sequence pRS1 (rape ACCase clone). pK111 (Wheat ACCase clone) was subjected to nested deletions by the recommended method (Pharmacia, "d.s. Nested Deletion Kit") and sequenced by a combination of forward and reverse primers and generated oligonucleotide priming. Computer analysis of DNA sequence was carried out using the SEQNET package from the SERC facility at Daresbury and DNA Strider.

3. Northern Blot Analysis

Poly A+mRNA was prepared from either 5 g young leaf or 5 g embryos harvested at 15, 22,29, 36, 42 and 49 days post anthesis using the recommended procedure (Pharmacia mRNA purification kit). 1–5 ug was loaded on to a 1% formamide/formaldehyde agarose gel for electrophoresis. The Northern blot procedure was as described previously Elborough et al 1994).

4. Southern Blot Analysis

Total DNA isolated from rape and Arabidopsis leaves (10 ug and 2 ug/digestion respectively) was digested with EcoR1, HindIII and BamHI separately for 8 Hrs. The DNA was separated by TAE agarose electrophoresis, blotted and hybridised to radiolabelled probe as described by Sammbrook et al.

RESULTS 1.1 Partial Purification of ACCase from Wheat Germ

Partial purification of Wheat ACCase was carried out essentially using the method previously described by Egin-Buhler et al (1980) with several modifications.

All operations were carried out at 4° C. unless otherwise stated. All buffers used contained 14 mM β-mercaptoethanol and 0.3 mM EDTA.

Figure 1B:
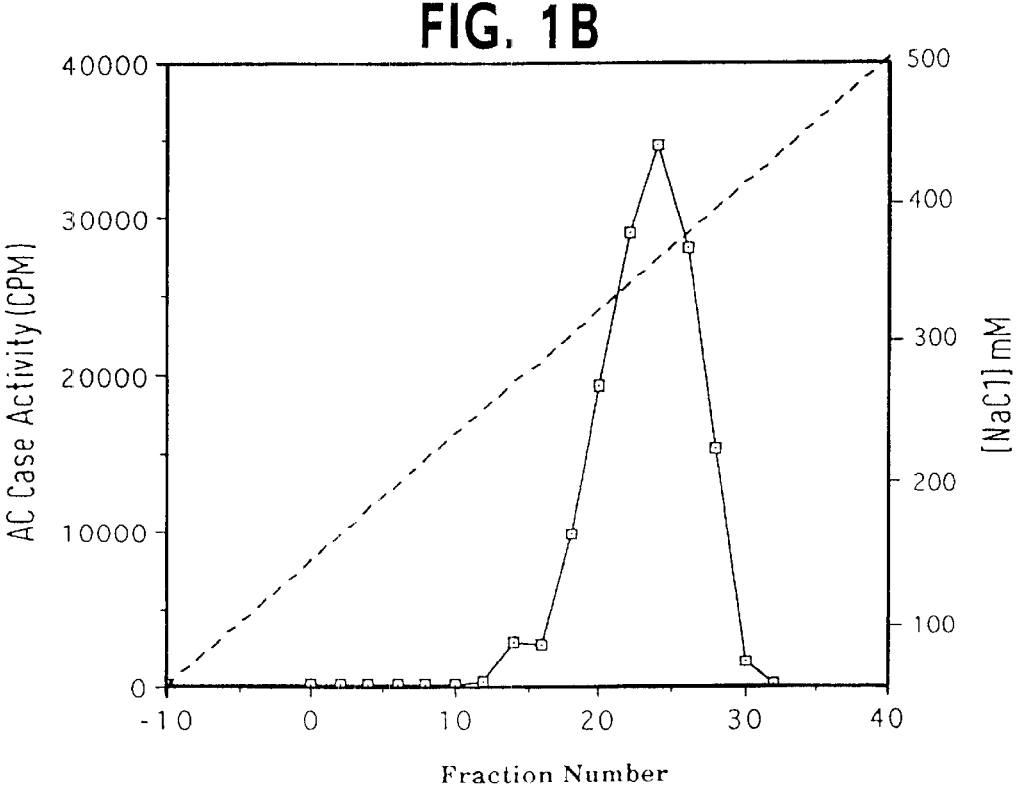

6×25 g of dry Avalon Wheat germ was ground in a coffee grinder for 15 secs. 200 ml 100 mM Tris-HCl pH 7.5 was added to each and polytroned on full speed for 1 minute. The homogenate was stirred for 15 minutes and spun at 20,000 g. The supernatant was stirred with 25 g wet weight Dowex 50 previously equilibrated with 100 mM Tris-HCl pH 7.5 for 15 minutes. The suspension was filtered through cheese cloth and 10% Polyethyleneimine at pH 7.5 added to 0.03% w/v dropwise whilst stirring. After 15 minutes the suspension was spun again at 20,000 g. Powdered $(NH_4)_2SO_4$ was added to a final saturation of 60% and stirred for 1 hour. After spinning at 20,000 g the pellets were resuspended in 100 ml 100 mM Tris-HCl pH 7.5/100 mM NaCl. The supernatant was dialysed for 1 hour against 5 litres 100 mM Tris-HCl pH 7.5/100 mM NaCl and subsequently overnight with fresh buffer (5 litres). Powdered $(NH_4)_2SO_4$ was added to a final saturation of 25% and stirred for 1 hour spun at 20,000 g and the supernatant brought up to 70% saturation. After centrifugation the resulting pellet was resuspended in 50 ml 20 mM Tris-ECl pH 7.5, 20 mM NaCl and dialysed with 3×1 hour changes against 5 litres 20 mM Tris-HCl pH 7.5, 20 mM NaCl/20% glycerol. The resultant suspension was diluted to a conductivity of <$4.3 \times 10^{-3}$ cm$^{-1}$ and stirred slowly with 150 ml of pre-equilibrated Q-sepharose (in 20 mM Tris-Hcl pH 7.5 20 mM NaCl/20% glycerol) for 2 hours. The unbound protein was removed using a sintered glass funnel and the matrix washed with 10 volumes of 20 mM Tris-HCl pH 7.5, 20 mM NaCl/20% glycerol. The slurry was packed into a 10 cm diameter Pharmacia column. Protein was eluted from the column using a gradient of 60–500 mM NaCl/20 mM Tris-HCl pH 7.5/20% glycerol (see FIG. 1A for elution profile) at 100 ml hr$^{-1}$ collecting approx 9 ml fractions. Every other fraction was assayed for ACCase activity, the most active fractions pooled and brought to 50% $(NH_4)_2SO_4$ saturation. The pellet after centrifugatior was taken up in a minimal volume (approx 100 ml) of 20 mM Tris-HCl pH 7.5, 5 mM MgCl, 20% glycerol to give >$4.6 \times 10^{-3}$ cm$^{-1}$ conductivity. This was incubated with 100 ml pre-equilibrated Blue-sepharose (in 20 mM Tris-HCl, pH 7.5/5 mM MgCl/20% glycerol) with mixing for 2 hours. The matrix was washed with 10 volumes of 20 mM Tris-HCl pH 7.5/5 mM MgCl/20% glycerol using a sintered glass funnel. The washed matrix was packed into a 10 cm diameter Pharmacia column and the protein eluted from the column with a 60–500 mM NaCl/20 mm Tris-HCl pH 7.5/5 mM MgCl/20% glycerol gradient (see FIG. 1B for elution profile) at 100 ml 1 hour taking 9 ml fractions. The pooled active fractions (post-Blue-sepharose material) were stored frozen at −70° C.

1.2 Identification of Approx. 220 kDa Protein as Biotin Containing

Figure 2A:
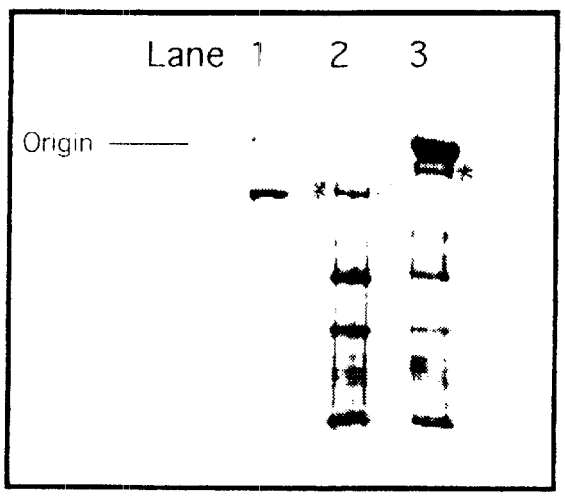
FIG. 2A shows an SDS PAGE gel of wheat embryo ACCaseshowing the alteration in mobility caused by the binding of streptavidin. Lane 1 contains 500 ng myosin (200 kDa); lane 2 contains 10 μl Post Blue-sepharose material without Streptavidin; and, lane 3 contains 10 μl Post Blue-sepharose material with streptavidin. ACCase is indicated by asterisks (*) at its normal migration and that of the ACCase/streptavidin complex respectively.

The dominant 220 kDa a band in the post Blue-sepharose material was identified as ACCase by both its ability to change mobility during SDS PAGE in the presence of streptavidin and its estimated molecular weight (Egin-Buhler et al. (1980). SDS PAGE ×5 loading buffer (5 μl) was added to 20 ul post Blue-sepharose material, boiled at 100° C. for 2 mins. and 1 μl of a 5 mM Steptavidin stock added immediately. The solution was incubated at 650° C. for 5 mins. and loaded onto an SDS PAGE gel next to myosin (Mr 200 kDa) and untreated post Blue-sepharose material sample for comparison (see FIG. 2A). Streptavidin clearly reduced the mobility of the 220 kDa band, indicating that it is biotin containing. The only known biotin enzyme with a MW of 220 kDa is ACCase.

1.3 Generation and Sequencing of Wheat ACCase Peptides

Figure 2B:
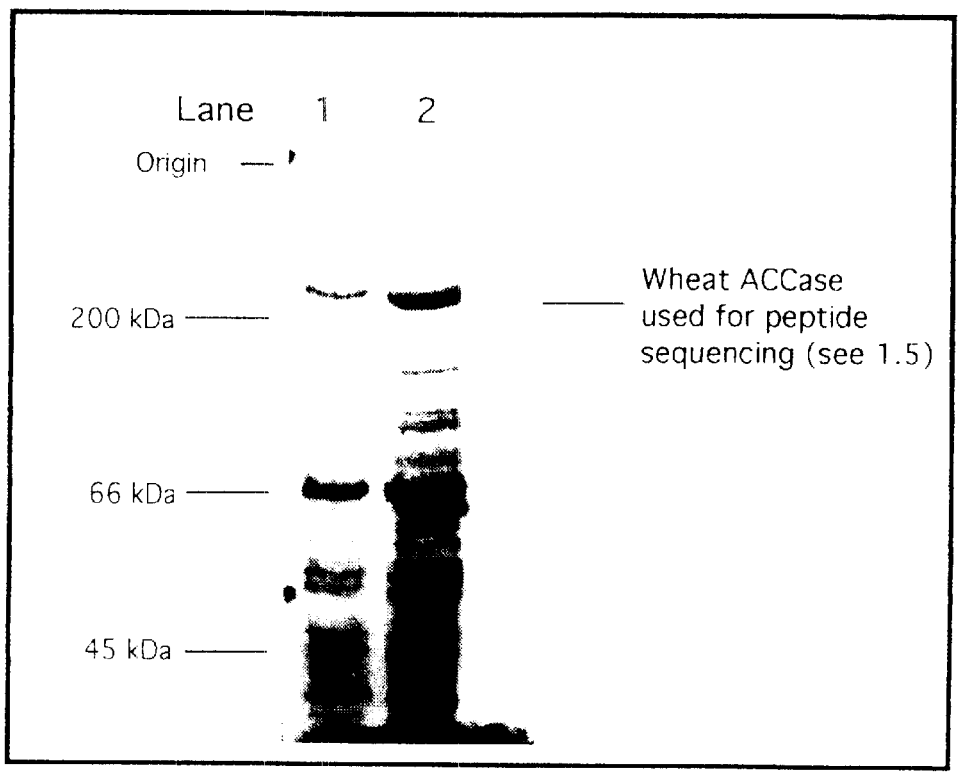
FIG. 2B shows an SDS PAGE gel of purified wheat embryo ACCase, with the 220 kd band taken for sequencing indicated. Lane 1 contains 1 μl Post Blue-sepharose material and lane 2 contains 10 μl Post Blue-sepharose material.

A sample of post-Blue sepharose material estimated to contain approx. 400 pM (80 μg) of ACCase, as determined by comparison with known concentration standards, was loaded onto an SDS PAGE prep gel (see 1.3 for method and FIG. 2B for appearance of sample). The running buffer was fresh and had a reduced level of SDS (0.035% SDS). Chromaphor green (Promega) was added at 1:1000 dilution to the upper tank during electrophoresis to allow the visualisation of protein. the ACCase protein band at approx. 220 kDa was cut out of the gel, frozen and stored at −20° C. overnight. The gel slices were trimmed of excess acrylamide and loaded on to one well of a 3 mm thick large Biorad Protean gel. The gel slices once loaded were overlaid with Endoproteinase LysC (Promega) at 6.5% protein concentration in 50% glycerol/0.125M Tris pH 6.8,/0.1%. SDS/3% B-mercaptoethanol/0.005% Bromophenol Blue. The gel was run until the protein was at the stacker interface at which point electrophoresis was stopped for 1 hr at room temperature. Electrophoresis was resumed until the dye front reached the bottom of the gel. Peptides were semi-dry blotted into ProBlot (Applied Biosystems Inc.) according to manufacturers instructions. Rapid Coomassie staining of the blot (according to ProBlot instructions) identified peptide fragments which were excised from the membrane and loaded onto an ABI 477A pulse liquid protein sequencer. Sequence data was obtained at an amino acid level of 10–20 pM (see FIG. 3).

Sequence data was obtained for 4 peptides, yielding stretches of N-terminal amino acid sequence of 17, 18, 9 and 20 amino acids (FIG. 3).

2. ACCase Clone Isolation and Sequencing 2.1 Wheat ACCase cDNA

A wheat cDNA library was probed with a 2.7 kb EcoR1 fragment, and a 1.54 kb HindIII fragment of the maize partial cDNA clone pA3 which contains 4.5 kb of the 3' maize ACCase. This yielded a 1.85 kb clone inserted between the Eco R1 and XhoI site in the multi cloning cassette of pSK. The DNA was recovered by plasmid rescue in the host strain DH5α. This clone was denoted pK111.

The nucleotide sequence data of this partial cDNA, with the derived amino acid sequence from the three reading frames is shown in FIG. 4.

FIG. 4 also shows that sections of pK111 show complete homology with the amino acid sequence of the 4 peptides isolated from the purified wheat germ enzyme, providing good evidennce that the cDNA does indeed code for wheat embryo ACCase.

Figure 5:
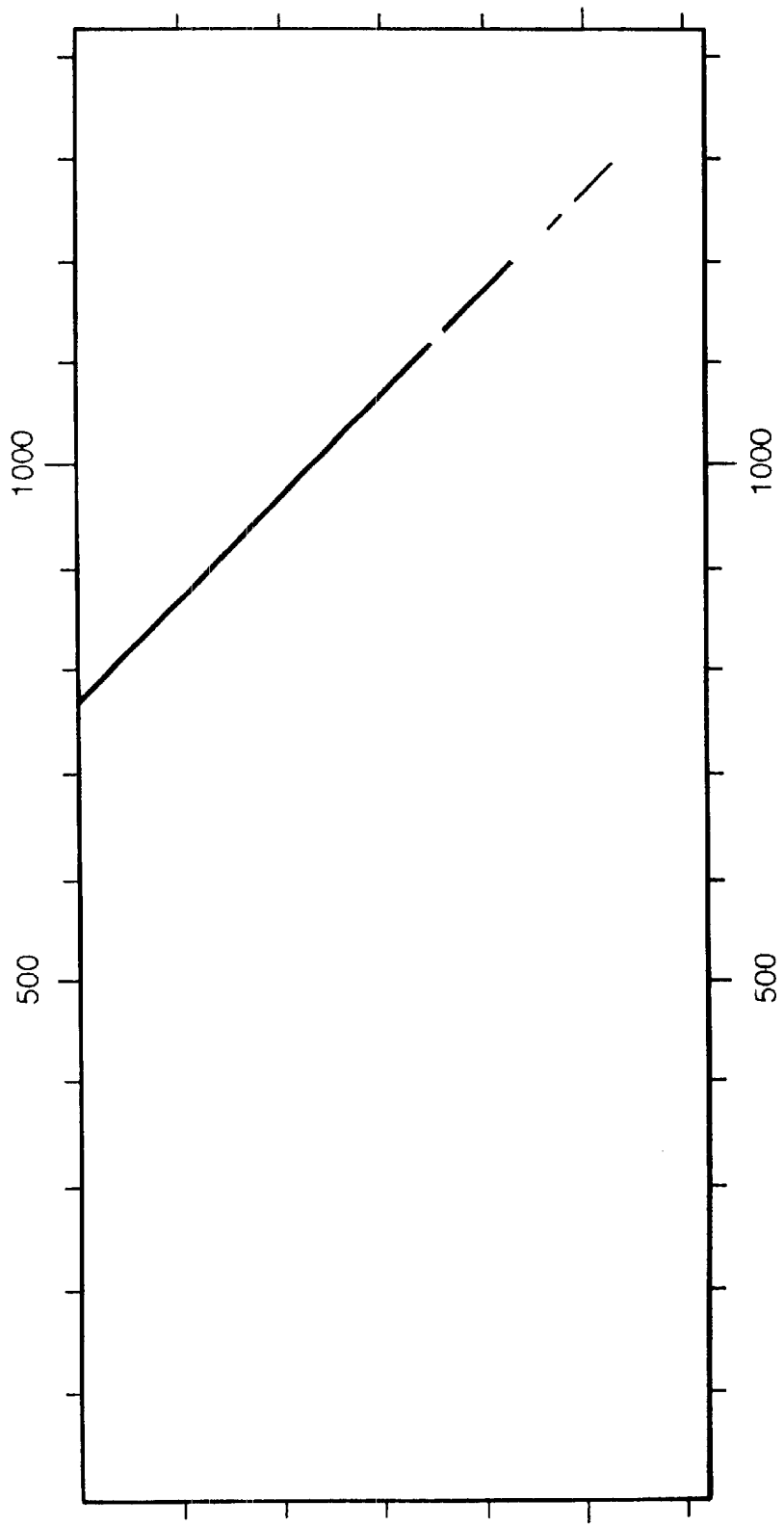
FIG. 5 shows a dot matrix plot of the deduced amino acid sequence of wheat ACCase clone pK111 against that of the maize ACCase clone pA3.

A dot matrix comparison of the deduced amino acid sequence from the largest open reading frame against that of the maize ACCase is presented in FIG. 5. pK111 showed 82.33% homology with the maize cDNA at the nucloetide level and 88.17% similarity/78.44% identity at the amino acid level.

In addition the deduced amino acid data of the wheat cDNA showed large homologous regions with the known sequences of rat (62%) and yeast (62%) ACCase.

2.2 Isolation of a Partial Rape ACCase cDNA Encoding the Transcarboxylase Domain Although ACCase has been purified from rape embryo, the amounts obtained were not amenable to protein sequencing. To study ACCase at the sequence level we needed to isolate its cDNA. A rape embryo derived poly dT primed λZapII library was screened with the partial wheat ACCase cDNA previously isolated. A hybridising cDNA of 2.5 kb was taken through three rounds of screening and plasmid rescued (pRS1). The clone was fully sequenced in both directions by a combination of nested deletions and dye primer sequencing. The cDNA sequence has been submitted to EMBL (Accession no. X77382). The predicted amino acid sequence from the largest open reading frame is shown in FIG. 6. Dot matrix analysis of the cDNA with previously described ACCase sequences showed it to be a partial clone of ACCase corresponding to the transcarboxylase domain (FIG. 7). The predicted amino sequence of the rape clone showed sequence identity/similarity levels of approximately 44/61% with the yeast (Al-Feel et al, 1992), rat (Lopez-Casillas et al, 1988) algae (Roessler and Ohlrogge, 1993) and the wheat ACCase cDNA pK111. Since the mRNA contaions a polyA tail and was obtained from the poly A fraction it is probable that the ACCase cDNA isolated was nuclear encoded.

2.3. Isolation of the Arabidopsis ACCase Genomic Clone and Further Rape cDNA Cloning The average insert size of our rape poly dT primed cDNA library, described above, was approximately 2–2.5 kb. Therefore it was unlikely that the library would contain much more 5' cDNA. To obtain more 5' sequence a random primed library from rape embryo mRNA was constructed. Having made a suitable library there were two strategies available for cloning more 5' cDNA i) screen using the 5' region of our cDNA, or; ii) screen using 5' probes from a genomic clone. We chose the second option. The strategy was to clone the ACCase genomic gene, identify the open reading frames by sequence comparison and generate specific probes by the use of PCR. Since Arabidopsis is related to rape and has a smaller genome we chose to obtain the genomic clone from Arabidopsis. Previous data from this laboratory had shown that Arabidopsis DNA sequences are highly homologous to those of rape (data not shown). Screening a λ FixII Arabidopsis genomic library with a 1.2 kb Xho1/Pst1 fragment of the rape ACCase cDNA pRS1 yielded two independent genomic clones which hybridised strongly to the pRS1 ACCase probe. These were denoted λAYE4 and λAYE8. λAYE8 was subcloned to produce two plasmids:pKLU81, a 5.3 kb subclone in the EcoR1 site of pGEM 3ZF+; and pKLS2, which was excised from the λ clone by a partial Sa11 digest and subcloned into pSK+.

The pKLU81 subclone, considered to be a partial length genomic clone, was partially sequenced-from the 5' and 3' ends. Therefore two sets of data are presented for the 5' and 3' sequences from the same clone. The nucleotide sequences, with the derived amiono acid sequences from the 3 reading frames are shown in FIGS. 8 and 9. A data base search (Swissprot) using the derived amino acid sequence from the 5' 0.56 kb DNA sequence showed 40% identity with chicken and rat ACCase (FIG. 10).

Figure 11A:
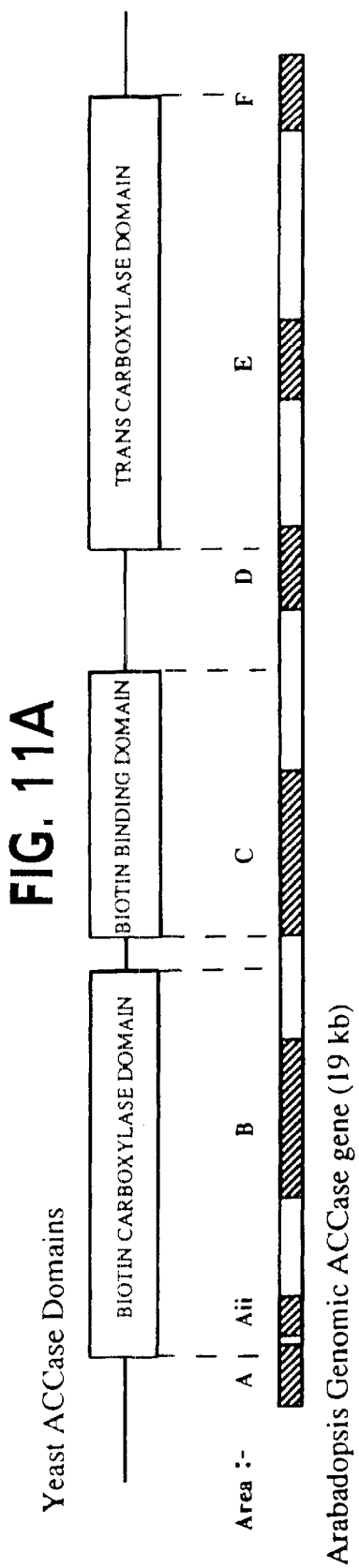
FIG. 11A is a schematic diagram showing the yeast ACCase domain orders relative to the sequenced regions (hatched boxes) of the Arabidopsis genomic clone. The areas of sequenced genomic clone are named A-F for easy identification in the text.

The genomic clone (pKLS2) was extensively subcloned through a combination of EcoRI/SalI/XbaI/HindIII digests, and partially sequenced by both Dye primer and Dye terminator chemistry. We found that intron-exon boundaries could not be allocated without cDNA data. We therefore opted to sequence only enough of the genomic clone to allow generation of open reading frame probes for cDNA screening. The full sequence data obtained is shown schematically in FIG. 11A (hatched areas A,Aii,B,C,D,E and F) and has been deposited with the EMBL data base (accession no's X77375–X77381).

Figure 11B:
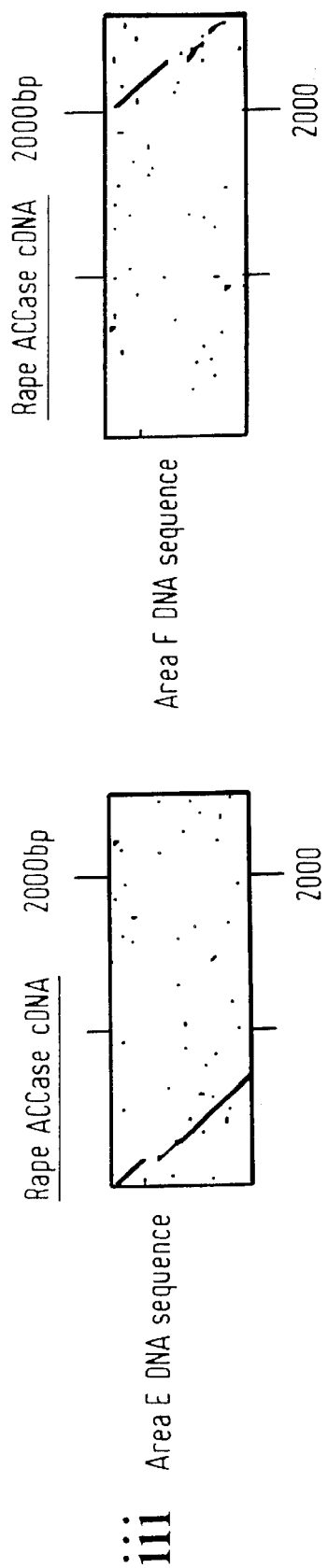
In FIG. 11Bi) the translated open reading frame (SEQ ID NO:20) from area Aii is shown in direct comparison with a region from the biotin carboxylase domain of yeast (SEQ ID NO:21). Boxed regions represent amino acid identity.

To map the ACCase activity domain order, within the genomic clone, the open reading frame sequences from the different sequenced areas were compared with the first two domains of the full length yeast cDNA (FIG. 11Bi and ii), and the rape transcarboxylase domain (FIG. 11Biii). Homology was sufficient to allow us to assign the same order of domains to the Arabidopsis gene as that of yeast ACCase shown in FIG. 11A ie: [Biotin carboxylase-Biotin binding-Transcarboxylase].

Sequence data from an open reading frame at the 5' end of the genomic clone (area Aii) showed a marked homology (49.5/64% identity/similarity at the derived amino acid level) with the 5' region of yeast ACCase (see FIG. 11Bi). The 3' end of the cloned genomic fragment (19 kb) was sequenced and shown to be homologous to the 3' end of the rape 2.5 kb cDNA clone isolated from the poly d'T primed mRNA library (FIG. 11Biii). Since we had approximately 1.3 kb 5' to area Aii we reasoned that it was likely that pKLS2 was the full length genomic clone. The pKLU 81 subclone was a partial length genomic clone corresponding to a portion of the sequence of pKLS2.

Figure 12B:
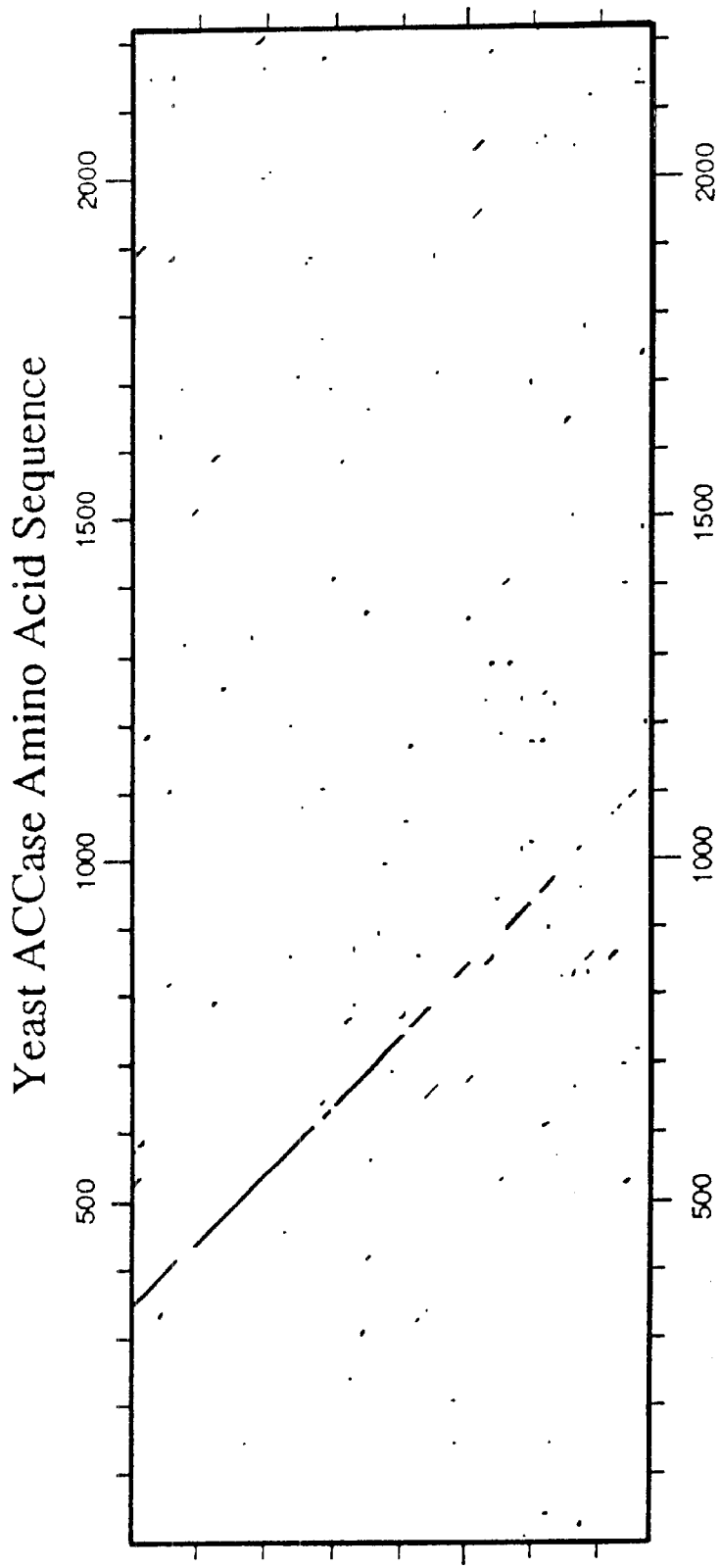
FIG. 12B shows the dot matrix comparison (DNA Strider, Stringency 9 Window 21) of derived rape ACCase amino acid sequence (biotin binding domain) against yeast ACCase.

Since the Arabidopsis genomic clone showed a high degree of homology to the rape cDNA isolated (86% identity in the exons of areas E and F) it was clear that the genomic clone could be used to isolate further-rape cDNA's. We generated a specific probe via PCR of area C within the genomic clone and used it to screen the random primed library generated from rape embryo mRNA. Two cDNA clones (pRS8 and pRS6 containing 2.0 kb and 1.1 kb cDNA respectively) were isolated and sequenced. The cDNA from each was shown to overlap. The full combined derived amino acid sequence (pRS8/6 2.38 kb cDNA size) is presented in FIG. 12Ai (EMBL accession no X77374). The sequence analysis of the clones showed significant homology with that of yeast (39/58% identity/similarity), rat (38/59% identity/similarity) and algal (34/54% identity/similarity) ACCase. Within the cDNA sequence is the highly conserved biotin binding site [Val-Met-Lys-Met], shown in FIG. 12Ai as the underlined region. Direct comparison with yeast biotin binding site is shown in FIG. 12Aii. Interestingly the sequence also showed homology at it's 5' end with the 3' portion of the yeast biotin carboxylase domain. This data demonstrated that the domain order in rape [Biotin carboxylase-Biotin binding-Transcarboxylase] is consistent with the domain assignment of Arabidopsis.

3. Southern Blot Analysis

Figure 13:
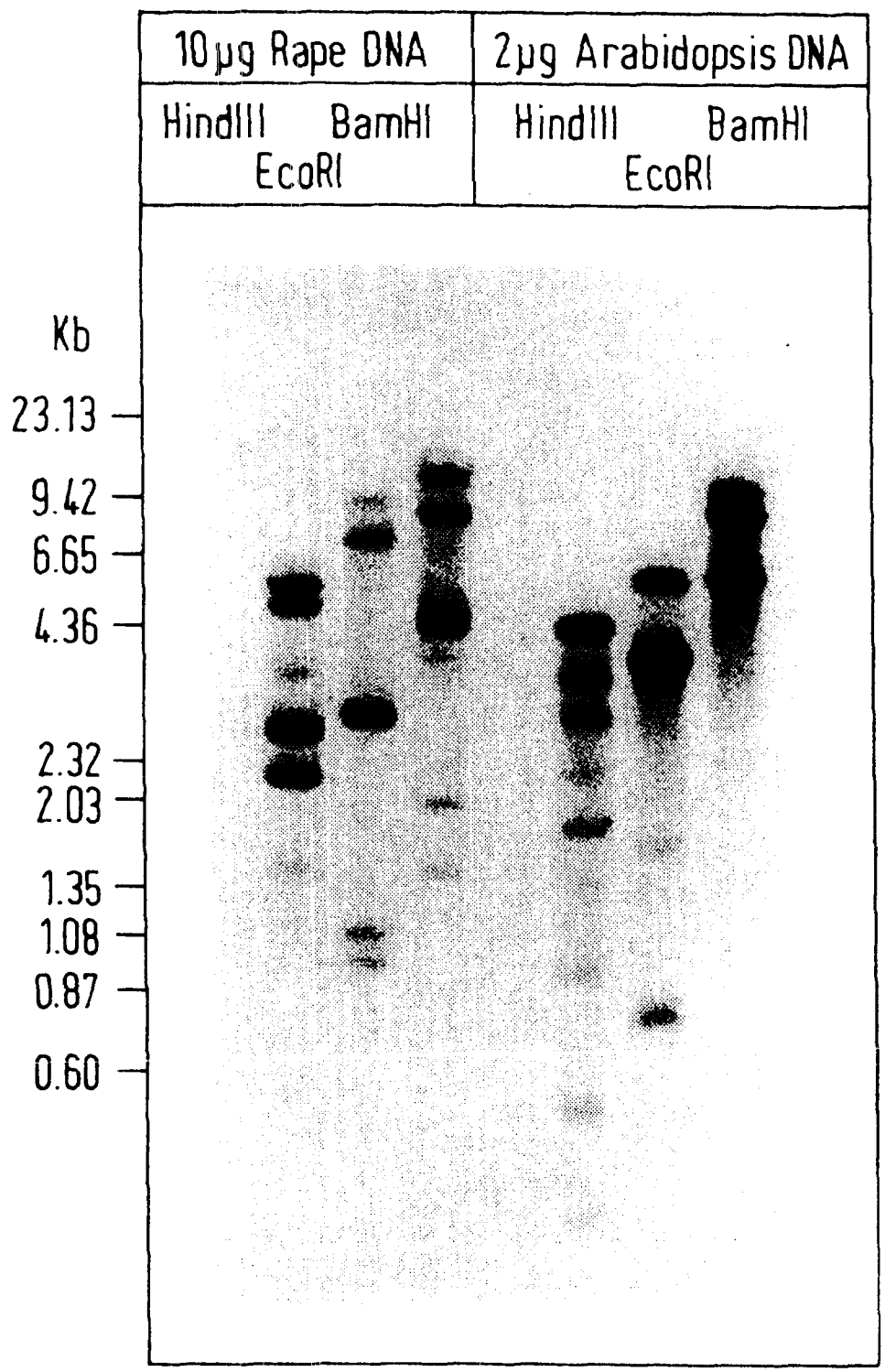
FIG. 13 shows ACCase Southern blot analyses of rape and Arabidopsis genomic DNA. Restrriction endonuclease digested DNA was hybridised to the Arabidopsis ACCase genomic clone by Southern blot. Hybridisation and washing conditions were carried out as described in materials and methods. The blot shown was exposed for 5 days, further exposure provided no extra information. Both λ HindIII and OX 174 HaeIII DNA markers (indicated on the left hand side) were run on the same 1% gel and viewed by ethidium bromide staining/UV.

Since it was not known how many genes for ACCase are present in rape and Arabidopsis, total DNA was analysed by Southern blotting. Both rape and Arabidopsis total DNA was digested with three separate restriction enzymes and blotted. The Arabidopsis genomic clone indicated that ACCase genes would most likely be relatively large. The size dictated that it was not possible, using partial cDNA's as probes, to gain an accurate estimate of the gene copy number by Southern blot. The blot was therefore hybridised to the full Arabidopsisg genomic clone 19 kb) labelled by random primed labelling. The sum of the Arabidopsis bands that hybrised to the probe was approximately 20 kb (FIG. 13). Since the genomic clone is approximately 19 kb, and showned a similar pattern when digested with the same enzymes (results not shown), we deduced that there is only the one gene present in Arabidopsis. Although the rape profile is more complicated it can be seen that it consists of a relatively small gene family (see FIG. 13).

4. Northern Blot Analysis

The expression of ACCase during rape embryonic development was examined by Northern blotting using the 2.5 kb rape cDNA clone as probe. The blotrs contained 5 ug rape poly A+mRNA prepared from a set of staged embryos taken from *Brassica napus Jet Neuf* at 15, 22, 29, 35,42 and 49 days post-anthesis. Embryos taken from the same seed set were also analysed for oil content to monitor development. The oil content data is presented (expressed as fatty acid/mg seed) graphically in FIG. 14A. The Northern blot was hybridised separately to three successive probes and stripped after each in preparation for the next probe. The three probes used-were embryo derived cDNAs for enoyl reductase (1.15 kb), βketo reductase (1.185 kb) and ACCase (2.5 kb). All three cDNAs were highly expressed in seed with maximum expression being coincidental at 29 days post-anthesis (FIG. 14A). However it appears that the initial onset of mRNA production occurs in the order enoyl reductase, βketo reductase and ACCase. The profile of all three genes expression during embryogenesis was reproducable in individually probed blots with peak expression occuring at 29 days. The sizes of the hybridising bands were 1.65, 1.7 and 7.5 kb respectively as determined by size markers run on the same agarose gel used for the blot. The level of the ACCase mRNA was relatively lower than that of enoyl reductase and βketoreductase. This may be in part due to the successive stripping of the blot and degradation of the large 7.5 kb message during handling.

Figure 14B:
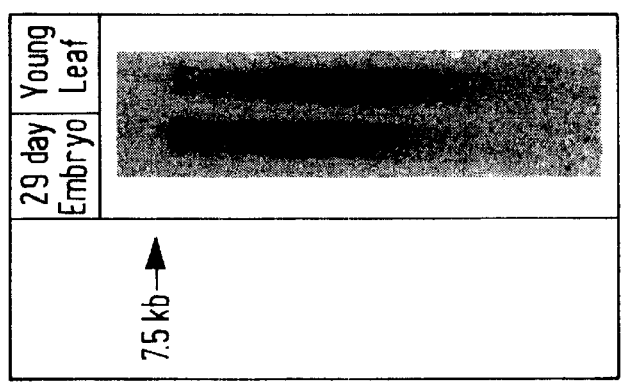
In FIG. 14B the probe used in the Northern blot shown was the rape transcarboxylase domain cDNA derived from an embryo library. 1 µg of poly A+RNA from 29 days post anthesis embryos and young leaf was used for the blot. Hybridisation and washing conditions were as in materials and methods. Exposure was for 7 days. Molecular weight markers were viewed by ethidium bromide/UV.
Figure 14A:
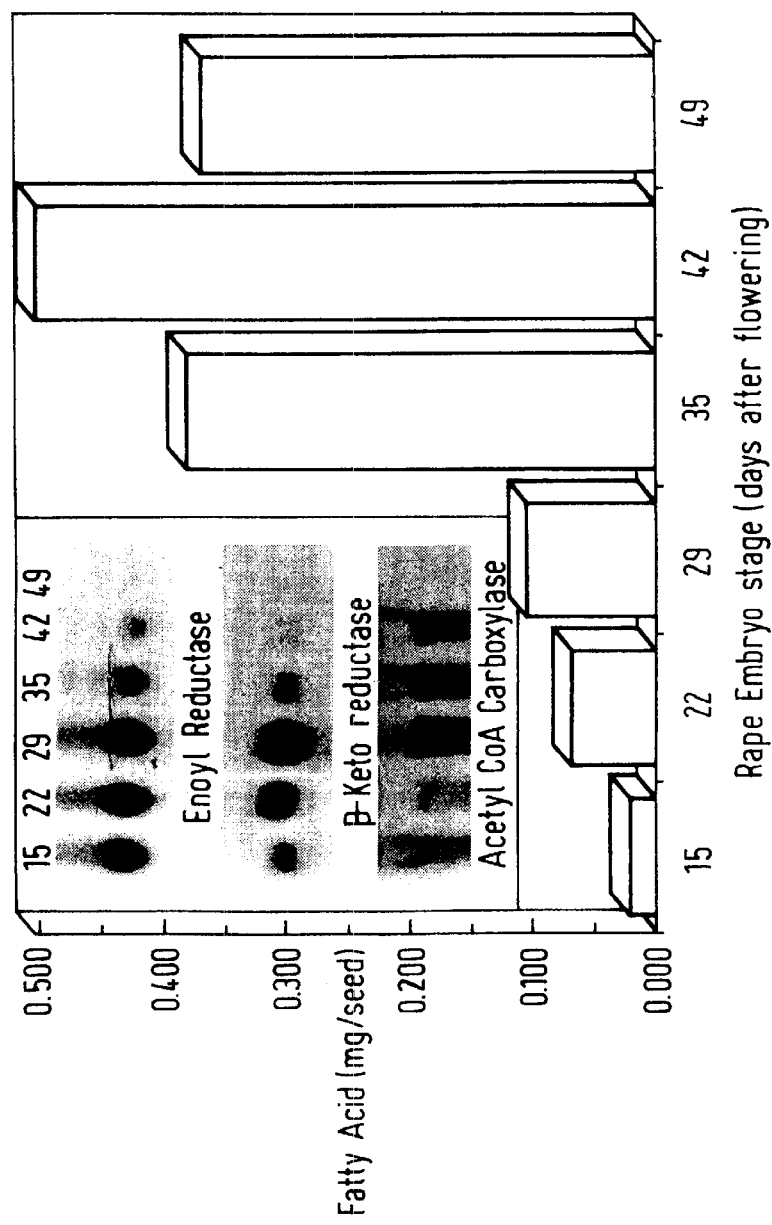
In FIG. 14A the graph shows the oil content as total fatty acid (mg/seed) in relation to the stage of rape embryogenesis. Details of the analysis method are presented in materials and methods. The three Northern blots shown, relating to the different stages of embryogenesis, are all derived from the same blot after successive stripping. The probes used were as indicated in the text and the amount of polyA+RNA was 5 µg for each stage. Hybridisation and washing conditions were as in materials and methods. Exposure was for 7 days.

A Northern blot comparison of ACCase expression in 29 days post-anthesis embryo and young leaf, using the embryo derived 2.5 kb cDNA as a probe is shown in FIG. 14B. The 7.5 kb band that hybridises was approximately five times more abundant in seed than in leaf, as might be expected for ACCase. The size of the full length mRNA (7.5 kb) was consistent with the known size of the full length mRNA for both maize and wheat ACCase.

References

Al-Feel, W., Chirala, S. S., Wakil, S. J. (1992) Proc. Natl. Acad. Sci. 89, 4534–4538.
Egin-Buhler, B et al (1980) Arch Biochem Biophys 203, 90–100.
Elborough et al (1994) Plant Mol. Biol. 24, 21–34.
Hellyer, A. et al (1986) Biochem Soc Trans 14, 565–568.
Laemmli (1970) Nature (Lond) 227, 680–685.
Logemann, J et al (1987) Anal. Biochem. 163, 16–20
Lopez-Casillas, F. et al (1988) Proc. Natl. Acad. Sci. 85, 5784–5788.
Roessler, P. G. and Ohlrogge, J. B. (1993) J. Biol Chem 268, 19254–19259
Sammbrook, J. (1989) "Molecular Cloning: A laboratory Manual" 2nd edition, CSH Laboratory Press

---

What is claimed is:

1. A partial cDNA insert specifying acetyl Coenzyme A carboxylase (ACCase), isolated from seed of *Brassica napus*, having the nucleotide sequence set forth in FIG. 6 (SEQ ID NO:12) or set forth in FIG. 12 (SEQ ID NO:32) or of the insert contained in the plasmid pRS1, which has been deposited in *Escherichia coli* under accession no. NCIMB 40555, and variations thereof permitted by the degeneracy of the genetic code which encode the amino acid sequence of the *Brassica napus* ACCase.

2. A partial cDNA specifying acetyl Coenzyme A carboxylase (ACCase), isolated from wheat germ, having the nucleotide sequence set forth in FIG. 4 (SEQ ID NO:9) or of the insert contained in the plasmid pK111, which has been deposited in *Escherichia coli* under accession no. NCIMB 40553, and variants thereof permitted by the degeneracy of the genetic code which encode the amino acid sequence of the wheat germ ACCase.

3. An isolated genomic DNA specifying acetyl Coenzyme A carboxylase (ACCase) from *Arabidopsis thaliana* having the nucleotide sequence set forth in FIG. 8 (SEQ ID NO:13) or of the insert contained in the plasmid pKLU81, which has been deposited in *Escherichia coli* under accession no. NCIMB 40554, and variants thereof permitted by the degeneracy of the genetic code which encode the amino acid sequence of the *Arabidopsis thaliana* ACCase.

4. A gene construct for use in transforming plants comprising a promoter active in plant cells, a structural region encoding mRNA in sense or antisense orientation to one or more domains of the ACCase gene and a 3' untranslated region, wherein said structural region is selected from the group consisting of SEQ ID NO:9, SEQ ID NO:12, SEQ ID NO:13 and SEQ ID NO:32.

5. A construct as claimed in claim 4 in which the promoter is a tissue-specific or developmentally regulated promoter.

6. A construct as claimed in claim 4 in which the promoter is the promoter of the napin gene of *Brassica napus*.

7. A method of transcribing the structural region of the gene construct as claimed in claim 4 comprising inducing the promoter of the gene construct and thereby transcribing the structural region which is in the sense orientation.

8. A method of transcribing the structural region of the gene construct as claimed in claim 4 comprising inducing the promoter of the gene construct and thereby transcribing the structural region which is in the antisense orientation.

9. A plant expression cassette comprising (i) a promoter recognized in a plant and (ii) a structural region encoding one or more domains of a plant acetyl Coenzyme A carboxylase (ACCase) enzyme, said structural region comprising the isolated partial cDNA of claim 1 or claim 2 or the isolated genomic DNA of claim 3.

10. A plant expression cassette as claimed in claim 9 in which the promoter is a tissue-specific or developmentally regulated promoter.

11. A plant expression cassette as claimed in claim 10 in which the promoter is a seed-specific promoter.

12. A method of transcribing the structural region of the expression cassette as claimed in claim 9 comprising inducing the promoter of the expression cassette and thereby transcribing the structural region, which encodes a full-length ACCase enzyme.

13. A method of transcribing the structural region of the expression cassette as claimed in claim 12, wherein the structural region is in the sense orientation relative to the promoter.

14. A method of transcribing the structural region of the expression cassette as claimed in claim 12, wherein the structural region is in the antisense orientation relative to the promoter.

15. A method of transcribing the structural region of the expression cassette as claimed in claim 9 comprising inducing the promoter of the expression cassette and thereby transcribing the structural region, which encodes a partial-length ACCase enzyme.

16. A method of transcribing the structural region of the expression cassette as claimed in claim 15, wherein the structural region is in the sense orientation relative to the promoter.

17. A method of transcribing the structural region of the expression cassette as claimed in claim 15, wherein the structural region is in the antisense orientation relative to the promoter.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
          (A) LENGTH: 17 amino acids
          (B) TYPE: amino acid
          (D) TOPOLOGY: linear (ii) MOLECULE TYPE: peptide (iii) HYPOTHETICAL: NO (v) FRAGMENT TYPE: internal (vi) ORIGINAL SOURCE:
          (A) ORGANISM: Avena sativa
          (B) STRAIN: Avalon (xi) SEQUENCE DESCRIPTION: SEQ ID NO:1:

Met Ala Thr Asn Gly Val Glu Xaa Leu Thr Val Ser Asp Asp Leu Glu
  1               5                  10                  15
Gly (2) INFORMATION FOR SEQ ID NO:2:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Avena sativa
        (D) DEVELOPMENTAL STAGE: Embryo (vii) IMMEDIATE SOURCE:
        (B) CLONE: pK111

(xi) SEQUENCE DESCRIPTION: SEQ ID NO:2:

Met Ala Thr Asn Gly Val Val His Leu Thr Val Ser Asp Asp Leu Glu
  1               5                  10                  15
Gly (2) INFORMATION FOR SEQ ID NO:3:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Avena sativa (xi) SEQUENCE DESCRIPTION: SEQ ID NO:3:

Leu Gly Gly Ile Pro Val Gly Val Ile Ala Val Glu Thr Gln Thr Xaa
  1               5                  10                  15
Asp Gln (2) INFORMATION FOR SEQ ID NO:4:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Avena sativa
        (D) DEVELOPMENTAL STAGE: Embryo (vii) IMMEDIATE SOURCE:

```
            (B) CLONE: pK111

(xi) SEQUENCE DESCRIPTION: SEQ ID NO:4:

Leu Gly Gly Ile Pro Val Gly Xaa Ile Ala Val Glu Thr Gln Thr Met
  1               5                  10                  15

Met Gln (2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Avena sativa (xi) SEQUENCE DESCRIPTION: SEQ ID NO:5:

Asn Val Leu Glu Pro Gln Gly His Leu
  1               5

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Avena sativa
        (D) DEVELOPMENTAL STAGE: embryo (vii) IMMEDIATE SOURCE:
        (B) CLONE: pK111

(xi) SEQUENCE DESCRIPTION: SEQ ID NO:6:

Asn Val Xaa Glu Xaa Gln Gly Leu Ile
  1               5

(2) INFORMATION FOR SEQ ID NO:7:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Avena sativa (xi) SEQUENCE DESCRIPTION: SEQ ID NO:7:

Ser Ile Glu Ala Arg Lys Lys Gln Leu Leu Pro Leu Tyr Thr Gln Ile
  1               5                  10                  15
```

```
Ala Ile Arg Phe
        20

(2) INFORMATION FOR SEQ ID NO:8:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Avena sativa
        (C) INDIVIDUAL ISOLATE: pK111
        (D) DEVELOPMENTAL STAGE: embryo (xi) SEQUENCE DESCRIPTION: SEQ ID NO:8:

Ser Ile Glu Pro Arg Lys Lys Gln Leu Leu Pro Leu Tyr Thr Gln Ile
 1               5                  10                  15

Ala Val Arg Phe
        20

(2) INFORMATION FOR SEQ ID NO:9:

(i) SEQUENCE CHARACTERISTICS:
        (A) LENGTH: 1926 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Avena sativa
        (B) STRAIN: Avalon
        (D) DEVELOPMENTAL STAGE: embryo (vii) IMMEDIATE SOURCE:
        (B) CLONE: pK111

(xi) SEQUENCE DESCRIPTION: SEQ ID NO:9:

GAGAACATAC ATGGAAGTGC TGCTATTGCC AGTGCCTATT CTAGGGCCTA TGAGGAGACA      60

TTTACGCTTA CATTTGTGAC TTGACGGACT GTTGGAATAG GAGCATATCT TGCTCGACTT     120

GGCATACGGT GCATACAGCG TACTGACCAG CCCATTATCC TAACCGGGTT CTCTGCTTTG     180

AACAAGCTTC TTGGCCGGGA AGTGTACAGC TCCCACATGC AGTTGGGTGG CCCCAAAATT     240

ATGGCGACAA ACGGTGTTGT CCATCTGACA GTTTCAGATG ACCTTGAAGG TGTGTCTAAT     300

ATATTGAGGT GGCTCAGCTA TGTTCCTGCC AACATTGGTG GACCTCTTCC TATTACAAAA     360

TCTTTGGACC CACCTGACAG ACCCGTTGCA TATATCCCTG AGAATACATG TGATCCTCGT     420

GCAGCCATCA GTGGCATTGA TGATAGCCAA GGGAAATGGT TGGGGGGCAT GTTCGACAAA     480

GACAGTTTTG TGGAGACATT TGAAGGATGG GCGAAGTCAG TAGTTACTGG CAGAGCGAAA     540

CTCGGAGGGA TTCCGGTGGG TGTNATAGCT GTGGAGACAC AGACTATGAT GCAGCTCATC     600

CCTGCTGATC CAGGGCAGCT TGATTCCCAT GAGCGGTCTG TTCCTCGTNC TGGGCAAGTN     660

TGGTTTCCAN ATTNANCTAC TAAGACAGCT CAAGCAATGC TGGACTTCAA CCGTNAAGGA     720
```

```
TTACCTCTNT TCATCCTTGC NAACTGGAGA GGCTTCTCTG GTGGGCAAAG AGATCTTTTT    780

AAAGGAATCC TTCAGGCTGG GTCAACAATT GTTGAGAACC TTAGGACATA CAATCAGCCT    840

GCCTTTGTAT ATATCCCCAA GGCTGCAGAG CTACGTGGAG GGGCTTGGGT CGTGATTGAT    900

AGCAAGATAA ATCCAGATCG ATTTGAGTTC TATGCTGAGA GGACTGCAAA GGGTAATGTT    960

CTNGAACCNC AAGGGTTGAT TGANATCAAN TTCAGGTCAG AGGAACTCCA AGAGTGCATG   1020

GGCAGGGTTG ACCCAGAATT GATAAATCTG AAGGCAAAAC TCCTGGGAGC AAAGCATGAC   1080

AATGGAAGTC TATCTGAGTC AGAATCCCTT CAGAAGAGCA TAGAACCCCG GAAGAAACAG   1140

TTGTTGCCTT TGTATACTCA AATTGCGGTG CGGTTTGCTG AATTGCATGA CACTTCCCTT   1200

AGAATGGCTN CTAAGGGTGT GATTAAGAAG GTTGTAGACT GGAAAGATTC TAGGTCTTTC   1260

TTCTACAAGA GATTACGGAG GAGGATATCC GAGGACGTTC TTGCAAAGGA AATTAGAGGT   1320

GTAAGTGGCA AGCAGTTCTC TCACCAATCA GCAATCGAGC TGATCCAGAA ATGGTACTTG   1380

GCTTCTAAGG GAGCTGAAGC AGCAAGCACT GAATGGGATG ATGACGATGC TTTTGTTGCC   1440

TGGAGGGAAA ACCCTGAAAA CTACCAGGAG TATATCAAAG AACTTAGGGC TCAAAGGGTA   1500

TCTCAGTTGC TCTCAGATGT TGCAGACTCC AGTCCAGATC TAGAAGCCTT GCCACAGGGT   1560

CTTTCTATGC TACTAGAGAA GATGGATCCC TCAAGGAGAG CACAGTTTGT TGAGGAAGTC   1620

AAGAAAGTCC TTAAATGATC AGATGATACC AACGCATCCA ATTCAGAATG TGCATGATAT   1680

CGGTTTCTCT TGAAGTACAT ATATAGANGG ATACTATTCG GCTGTAACCG ACCATAGCTG   1740

ATCTGAGTCA ACCATTATTT TGTAAAACTT TTTTGCGGTC TTCTCTGTTA TTCGAGGCAA   1800

AACTTGTTTT CGGACGGCTC CGAATGGTTG ATGAGTGTAG TTGGAAAAAA AGCGGCCGGA   1860

ATTNCTGCAG CCCGGGGGAT CCNCTAGTTC TAGAGCGGCC GCACCGGGTT GGAGNTCCAG   1920

TTTTTT                                                              1926
```

(2) INFORMATION FOR SEQ ID NO:10:

(i) SEQUENCE CHARACTERISTICS:
        (A) LENGTH: 642 amino acids
        (B) TYPE: amino acid
        (D) TOPOLOGY: linear (ii) MOLECULE TYPE: protein (iii) HYPOTHETICAL: YES (v) FRAGMENT TYPE: N-terminal (vi) ORIGINAL SOURCE:
        (A) ORGANISM: Avena sativa
        (B) STRAIN: Avalon
        (D) DEVELOPMENTAL STAGE: embryo (vii) IMMEDIATE SOURCE:
        (B) CLONE: pK111

(ix) FEATURE:
        (A) NAME/KEY: Region
        (B) LOCATION: 81..97

(ix) FEATURE:
        (A) NAME/KEY: Region
        (B) LOCATION: 181..198

(ix) FEATURE:
        (A) NAME/KEY: Region
        (B) LOCATION: 319..327

(ix) FEATURE:
        (A) NAME/KEY: Region
        (B) LOCATION: 373..392

(xi) SEQUENCE DESCRIPTION: SEQ ID NO:10:

```
Glu Asn Ile His Gly Ser Ala Ile Ala Ser Ala Tyr Ser Arg Ala
 1               5                  10                  15

Tyr Glu Glu Thr Phe Thr Leu Thr Phe Val Thr Xaa Arg Thr Val Gly
                20                  25                  30

Ile Gly Ala Tyr Leu Ala Arg Leu Gly Ile Arg Cys Ile Gln Arg Thr
            35                  40                  45

Asp Gln Pro Ile Ile Leu Thr Gly Phe Ser Ala Leu Asn Lys Leu Leu
        50                  55                  60

Gly Arg Glu Val Tyr Ser Ser His Met Gln Leu Gly Pro Lys Ile
 65                 70                  75                  80

Met Ala Thr Asn Gly Val Val His Leu Thr Val Ser Asp Asp Leu Glu
                85                  90                  95

Gly Val Ser Asn Ile Leu Arg Trp Leu Ser Tyr Val Pro Ala Asn Ile
            100                 105                 110

Gly Gly Pro Leu Pro Ile Thr Lys Ser Leu Asp Pro Asp Arg Pro
        115                 120                 125

Val Ala Tyr Ile Pro Glu Asn Thr Cys Asp Pro Arg Ala Ala Ile Ser
130                 135                 140

Gly Ile Asp Asp Ser Gln Gly Lys Trp Leu Gly Gly Met Phe Asp Lys
145                 150                 155                 160

Asp Ser Phe Val Glu Thr Phe Glu Gly Trp Ala Lys Ser Val Val Thr
                165                 170                 175

Gly Arg Ala Lys Leu Gly Gly Ile Pro Val Gly Xaa Ile Ala Val Glu
            180                 185                 190

Thr Gln Thr Met Met Gln Leu Ile Pro Ala Asp Pro Gly Gln Leu Asp
        195                 200                 205

Ser His Glu Arg Ser Val Pro Arg Xaa Gly Gln Xaa Trp Phe Pro Xaa
    210                 215                 220

Xaa Xaa Thr Lys Thr Ala Gln Ala Met Leu Asp Phe Asn Arg Xaa Gly
225                 230                 235                 240

Leu Pro Xaa Phe Ile Leu Xaa Asn Trp Arg Gly Phe Ser Gly Gly Gln
                245                 250                 255

Arg Asp Leu Phe Lys Gly Ile Leu Gln Ala Gly Ser Thr Ile Val Glu
            260                 265                 270

Asn Leu Arg Thr Tyr Asn Gln Pro Ala Phe Val Tyr Ile Pro Lys Ala
        275                 280                 285

Ala Glu Leu Arg Gly Gly Ala Trp Val Val Ile Asp Ser Lys Ile Asn
    290                 295                 300

Pro Asp Arg Phe Glu Phe Tyr Ala Glu Arg Thr Ala Lys Gly Asn Val
305                 310                 315                 320

Xaa Glu Xaa Gln Gly Leu Ile Xaa Ile Xaa Phe Arg Ser Glu Glu Leu
                325                 330                 335

Gln Glu Cys Met Gly Arg Val Asp Pro Glu Leu Ile Asn Leu Lys Ala
            340                 345                 350

Lys Leu Leu Gly Ala Lys His Asp Asn Gly Ser Leu Ser Glu Ser Glu
        355                 360                 365

Ser Leu Gln Lys Ser Ile Glu Pro Arg Lys Lys Gln Leu Leu Pro Leu
    370                 375                 380

Tyr Thr Gln Ile Ala Val Arg Phe Ala Glu Leu His Asp Thr Ser Leu
385                 390                 395                 400

Arg Met Ala Xaa Lys Gly Val Ile Lys Lys Val Val Asp Trp Lys Asp
```

-continued

```
                      405                 410                 415
Ser Arg Ser Phe Phe Tyr Lys Arg Leu Arg Arg Ile Ser Glu Asp
                420                 425                 430
Val Leu Ala Lys Glu Ile Arg Gly Val Ser Gly Lys Gln Phe Ser His
                435                 440                 445
Gln Ser Ala Ile Glu Leu Ile Gln Lys Trp Tyr Leu Ala Ser Lys Gly
    450                 455                 460
Ala Glu Ala Ala Ser Thr Glu Trp Asp Asp Asp Ala Phe Val Ala
465                 470                 475                 480
Trp Arg Glu Asn Pro Glu Asn Tyr Gln Glu Tyr Ile Lys Glu Leu Arg
                485                 490                 495
Ala Gln Arg Val Ser Gln Leu Leu Ser Asp Val Ala Asp Ser Ser Pro
                500                 505                 510
Asp Leu Glu Ala Leu Pro Gln Gly Leu Ser Met Leu Leu Glu Lys Met
                515                 520                 525
Asp Pro Ser Arg Arg Ala Gln Phe Val Glu Glu Val Lys Lys Val Leu
                530                 535                 540
Lys Xaa Ser Asp Asp Thr Asn Ala Ser Asn Ser Glu Cys Ala Xaa Tyr
545                 550                 555                 560
Arg Phe Leu Leu Lys Tyr Ile Tyr Arg Xaa Ile Leu Phe Gly Cys Asn
                565                 570                 575
Arg Pro Xaa Leu Ile Xaa Val Asn His Tyr Phe Val Lys Leu Phe Cys
                580                 585                 590
Gly Leu Leu Cys Tyr Ser Arg Gln Asn Leu Phe Ser Asp Gly Ser Glu
                595                 600                 605
Trp Leu Met Ser Val Val Gly Lys Lys Ala Ala Gly Ile Xaa Ala Ala
    610                 615                 620
Arg Gly Ile Xaa Xaa Phe Xaa Ser Gly Arg Thr Gly Leu Glu Xaa Gln
625                 630                 635                 640
Phe Phe
```

(2) INFORMATION FOR SEQ ID NO:11:

(i) SEQUENCE CHARACTERISTICS:
        (A) LENGTH: 765 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Brassica napus (xi) SEQUENCE DESCRIPTION: SEQ ID NO:11:

```
Ala Arg Gly Arg Asn Ser Leu Ile Tyr His Ser Ile Thr Lys Lys Gly
1               5                   10                  15
Pro Leu His Gly Thr Gln Ile Asn Asp Gln Tyr Lys Pro Leu Gly Tyr
                20                  25                  30
Leu Asp Arg Gln Arg Leu Ala Ala Arg Arg Ser Asn Thr Thr Tyr Cys
            35                  40                  45
Tyr Asp Phe Pro Leu Ala Phe Glu Thr Ala Leu Glu Gln Phe Gly His
    50                  55                  60
```

-continued

Tyr Asn Asn Arg Glu Leu Arg Asn His Ala Arg Val Leu Leu Ser Val
 65                  70                  75                  80

Leu Lys Ser Leu Tyr Ser Pro Ile Ser Glu Gly Thr Ser Leu Met Pro
             85                  90                  95

Val Glu Arg Ser Pro Gly Leu Asn Glu Phe Gly Met Val Ala Trp Ser
            100                 105                 110

Leu Glu Met Ser Thr Pro Glu Phe Pro Met Gly Arg Lys Leu Leu Ile
        115                 120                 125

Val Ala Asn Asp Val Thr Phe Lys Ala Gly Ser Phe Gly Pro Arg Glu
        130                 135                 140

Asp Ala Phe Phe Leu Ala Val Thr Glu Leu Ala Cys Pro Lys Lys Leu
145                 150                 155                 160

Pro Leu Ile Tyr Leu Ala Pro Asn Ser Gly Ala Arg Leu Gly Val Ala
                165                 170                 175

Glu Glu Ile Lys Ala Cys Phe Lys Val Gly Trp Ser Asp Glu Val Ser
            180                 185                 190

Pro Glu Asn Gly Phe Gln Tyr Ile Tyr Leu Ser Pro Glu Asp His Ala
        195                 200                 205

Arg Ile Gly Ser Ser Val Ile Ala His Glu Ile Lys Leu Pro Ser Gly
210                 215                 220

Glu Thr Arg Trp Val Ile Asp Thr Ile Val Gly Lys Glu Asp Gly Ile
225                 230                 235                 240

Gly Val Glu Asn Leu Thr Gly Ser Gly Pro Ile Ala Gly Ala Tyr Ser
                245                 250                 255

Arg Ala Tyr Asn Glu Thr Phe Thr Leu Thr Phe Val Ser Gly Arg Thr
            260                 265                 270

Val Gly Ile Gly Ala Tyr Leu Ala Pro Leu Gly Met Arg Cys Ile Gln
        275                 280                 285

Arg Leu Asp Gln Pro Ile Ile Leu Thr Gly Phe Ser Thr Leu Asn Lys
        290                 295                 300

Leu Leu Gly Arg Glu Val Tyr Ser Ser His Met Gln Leu Gly Gly Pro
305                 310                 315                 320

Lys Ile Met Gly Thr Asn Gly Val Val His Leu Thr Val Ser Asp Asp
                325                 330                 335

Leu Glu Gly Val Ser Ala Ile Leu Asp Trp Leu Ser Tyr Ile Pro Ala
            340                 345                 350

Tyr Val Gly Gly Pro Leu Pro Val Leu Ala Pro Leu Asp Pro Pro Asp
        355                 360                 365

Arg Thr Val Glu Tyr Val Pro Glu Asn Ser Cys Asp Pro Arg Ala Ala
        370                 375                 380

Ile Ala Gly Val Asn Asp Asn Thr Gly Lys Trp Leu Gly Gly Ile Phe
385                 390                 395                 400

Asp Lys Asn Ser Phe Ile Glu Thr Leu Glu Gly Trp Ala Arg Thr Val
                405                 410                 415

Val Thr Gly Arg Ala Lys Leu Gly Gly Ile Pro Val Gly Val Val Ala
            420                 425                 430

Val Glu Thr Gln Thr Val Met Gln Ile Ile Pro Ala Asp Pro Gly Gln
        435                 440                 445

Leu Asp Ser His Glu Arg Val Val Pro Gln Ala Gly Gln Val Trp Phe
        450                 455                 460

Pro Asp Ser Ala Gly Lys Thr Ala Gln Ala Leu Met Asp Phe Thr Arg
465                 470                 475                 480

```
Lys Ser Phe His Cys Leu Ser Leu Arg Thr Gly Glu Gly Phe Gln Val
                485                 490                 495

Gly Arg Glu Ile Phe Ser Lys Glu Tyr Phe Arg Gln Val Ala Thr Ile
                500                 505                 510

Val Glu Asn Leu Arg Thr Tyr Arg Gln Pro Val Phe Val Tyr Ile Pro
                515                 520                 525

Lys Met Gly Glu Leu Arg Gly Gly Ala Trp Val Val Asp Ser Gln
530                 535                 540

Ile Asn Ser Asp Tyr Val Glu Met Tyr Ala Asp Glu Thr Ala Arg Gly
545                 550                 555                 560

Asn Val Leu Glu Pro Glu Gly Thr Ile Glu Ile Lys Phe Arg Thr Lys
                565                 570                 575

Glu Met Leu Glu Cys Met Gly Arg Leu Asp Pro Lys Leu Ile Asp Leu
                580                 585                 590

Lys Ala Arg Leu Gln Asp Pro Asn Gln Ser Glu Ala Tyr Thr Asn Ile
                595                 600                 605

Glu Leu Leu Gln Gln Gln Ile Lys Ala Arg Glu Lys Leu Leu Leu Pro
                610                 615                 620

Val Tyr Ile Gln Ile Ala Thr Lys Phe Ala Glu Leu His Asp Thr Ser
625                 630                 635                 640

Met Arg Met Thr Ala Lys Gly Val Ile Lys Met Cys Val Glu Trp Ile
                645                 650                 655

Gly Ser Arg Ser Phe Phe Tyr Lys Lys Leu Asn Arg Arg Ile Ala Glu
                660                 665                 670

Asn Ser Leu Val Lys Asn Val Arg Glu Ala Ser Gly Asp Asp Leu Ser
                675                 680                 685

Tyr Lys Ser Ala Met Gly Leu Ile Gln Asp Trp Phe Ser Lys Ser Asp
                690                 695                 700

Ile Pro Lys Gly Lys Glu Glu Ala Trp Thr Asp Asp Gln Val Phe Phe
705                 710                 715                 720

Thr Trp Lys Asp Asn Val Ser Asn Tyr Glu Leu Asn Leu Ser Glu Leu
                725                 730                 735

Arg Pro Gln Lys Leu Leu Asn Pro Thr Cys Arg Asp Trp Lys Phe Arg
                740                 745                 750

Arg Ile Tyr Arg Arg Cys His Lys Asp Leu Pro Ile Phe
                755                 760                 765

(2) INFORMATION FOR SEQ ID NO:12:

(i) SEQUENCE CHARACTERISTICS:
        (A) LENGTH: 2536 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Brassica napus
        (D) DEVELOPMENTAL STAGE: embryo (vii) IMMEDIATE SOURCE:
        (A) LIBRARY: poly dT primed lambda ZapII
        (B) CLONE: pRS1

(xi) SEQUENCE DESCRIPTION: SEQ ID NO:12:
```

```
GCACGAGGGA GAAACAGTTT GATTTACCAC TCAATTACCA AGAAGGGACC TTTGCATGGA      60

ACCCAAATCA ATGATCAATA TAAGCCACTG GGATATCTTG ACAGGCAACG TCTAGCCGCA     120

AGGAGGAGTA ACACTACATA TTGCTATGAC TTCCCGTTGG CATTTGAGAC AGCCTTGGAG     180

CAGTTTGGGC ATTACAACAA CCGGGAGTTA AGAAACCATG CAAGGGTACT CTTATCAGTG     240

CTAAAGAGCT TGTATTCTCC AATTTCAGAA GGTACATCTC TTATGCCAGT TGAAAGATCA     300

CCGGGTCTCA ATGAGTTTGG AATGGTGGCC TGGAGCCTAG AGATGTCGAC TCCTGAGTTT     360

CCTATGGGAC GGAAGCTTCT CATAGTCGCC AATGATGTCA CCTTCAAAGC TGGTTCTTTT     420

GGTCCTAGAG AGGACGCGTT TTTCCTTGCC GTGACTGAAC TCGCATGTCC CAAGAAGCTT     480

CCCTTGATTT ACTTGGCACC AAATTCTGGT GCCAGACTCG GAGTAGCTGA AGAAATCAAA     540

GCCTGCTTTA AAGTTGGATG GTCGGATGAA GTTTCCCCCG AAAATGGTTT TCAGTATATA     600

TACCTAAGCC CTGAAGACCA TGCAAGGATT GGATCATCTG TCATTGCGCA CGAAATAAAG     660

CTCCCTAGTG GGAAACAAG GTGGGTGATT GATACAATCG TTGGTAAAGA AGATGGTATT      720

GGTGTAGAGA ATCTAACCGG AAGTGGGCCA ATAGCGGGCG CTTACTCGAG GGCATACAAC     780

GAAACATTTA CTTTGACCTT TGTTAGTGGA AGAACGGTAG GAATTGGTGC TTACCTTGCC     840

CCCCTTGGTA TGCGGTGTAT ACAGAGACTT GACCAGCCGA TCATATTGAC TGGCTTTTCT     900

ACGCTCAACA AGTTACTTGG GCGTGAGGTC TATAGCTCTC ACATGCAACT TGGTGGCCCG     960

AAAATCATGG GCACAAATGG TGTTGTTCAT CTTACAGTCT CAGATGATCT CGAAGGTGTA    1020

TCAGCGATTC TCGACTGGCT GAGCTACATT CCTGCTTACG TTGGTGGTCC TCTTCCTGTT    1080

CTTGCCCCGT TAGACCCACC GGACAGAACC GTGGAGTACG TTCCAGAGAA CTCTTGCGAC    1140

CCGCGAGCTG CTATAGCTGG GGTTAACGAC AATACCGGTA AATGGCTTGG CGGTATCTTT    1200

GATAAAAATA GCTTTATTGA GACTCTTGAA GGCTGGGCAA GAACGGTAGT GACTGGTAGA    1260

GCTAAACTAG GGGGAATACC TGTAGGAGTT GTTGCGGTTG AGACACAGAC AGTAATGCAG    1320

ATCATCCCAG CAGATCCAGG ACAGCTCGAC TCTCATGAAA GAGTGGTTCC ACAGGCAGGG    1380

CAAGTCTGGT TTCCTGATTC TGCGGGCAAG ACAGCTCAAG CGCTCATGGA TTTCACAAGG    1440

AAGAGCTTCC ATTGTTTATC CTTGCGAACT GGAGAGGGTT TTCAGGTGGG CAGAGAGATC    1500

TTTTCGAAGG AATACTTCAG GCAGGTTGCG ACTATTGTAG AAAATCTGAG AACGTATCGG    1560

CAGCCAGTGT TTGTGTACAT CCCTAAGATG GGAGAGTTGC GAGGTGGAGC GTGGGTTGTT    1620

GTTGATAGCC AAATAAATTC AGATTATGTT GAAATGTATG CTGATGAAAC TGCTAGGGGG    1680

AATGTGCTTG AGCCAGAAGG AACGATAGAG ATAAAATTTA GAACGAAAGA GATGTTAGAG    1740

TGCATGGGAA GGTTAGACCC GAAGCTAATC GATCTCAAAG CAAGACTGCA AGATCCCAAC    1800

CAAAGTGAGG CTTATACAAA TATCGAGCTC CTCCAGCAAC AGATTAAAGC CCGAGAGAAG    1860

CTTCTCTTAC CAGTTTATAT CCAAATCGCC ACCAAATTTG CGGAACTTCA CGATACTTCC    1920

ATGAGAATGA CTGCCAAAGG AGTGATCAAA ATGTGTGTGG AGTGGATCGG CTCGAGGTCC    1980

TTCTTCTATA AGAAGCTCAA CCGGAGAATT GCTGAGAACT CTCTTGTGAA AAACGTAAGA    2040

GAAGCTTCAG GAGACGACTT ATCGTATAAA TCTGCAATGG GTTTAATTCA GGATTGGTTC    2100

TCCAAATCTG ACATTCCAAA GGGGAAAGAA GAAGCTTGGA CAGACGACCA AGTGTTCTTT    2160

ACATGGAAGG ACAACGTTAG TAACTACGAG TTGAATCTGA GCGAATTGAG ACCGCAGAAA    2220

CTGTTGAACC CAACTTGCAG AGATTGGAAA TTCCGTCGGA TCTATCGGCG CTGCCACAAG    2280

GACTTGCCAA TCTTCTAAAC AAGGTGGAGC CTTCAAGAAG AGAAGAGCTT GTTGAAGCGC    2340

TACGAAAAGT GTTAGGTTGA TGTACAAGAG GTCAAGCTTG TGACCCGAGA AAGATGGTCC    2400
```

```
TTTGGTGTTG CTTGTGTCCT ACGGTGAAAG AAGCTAGTTG GAAATTAGAT GTGGTCTTTC      2460

TTTCTTAAAT GTGTTGGCCC GAGCTGTAAA TGTTGTTGTA GCGTATAAGT GAGAATTGCG      2520

TAATAATTTA TTCAAC                                                     2536
```

(2) INFORMATION FOR SEQ ID NO:13:

(i) SEQUENCE CHARACTERISTICS:
        (A) LENGTH: 565 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (A) LIBRARY: lambda FixII type
        (B) CLONE: pKLU81

(xi) SEQUENCE DESCRIPTION: SEQ ID NO:13:

```
CTCTCTGGCA AATCCCTGGT ATAATCTACG TCCTTATTTC TTACAGGCAG CGGTTCCTCT       60

TCTTTATCCA TGCACACGAA TAATGTACTG TCTGTTTCTC TTTAATTTCG TAGAGATAAG      120

ACGGTTCTAT GGAATAGAAC ATGGTGGAGG TTATGATTCT TGGCGAAAAA CATCTGTTGT      180

AGCCTTCCCT TTTGATTTTG ATAAAGCTCA ATCTATAAGG CCAAAAGGTC ATTGTGTGGC      240

TGTACGTGTG ACAAGTGAGG TATCCTGATG ACGGGTTCAA ACCAACCAGC GGTAGAGTTC      300

AGGTAATGTG ATATCTGTGG AATGCAAAGT GAAAGTTCAT TCACTGAGGA ACTCTGTGGG      360

GTAACACTTG TATGAACTTG CAACAGGNGT TGAGTTTTAA GAGCAAGCCA AATGTGTGGG      420

CGTACTTCTC TGTCAAGGTA ATTTATATCT ATAGNGNCTC TGCTATATAA GTGTTTCACA      480

ATGNTTTAAT TTTNCGGCTA CTTTTTTACA GCTGTGGGGC ACCCGNGTCT TGGTTCCATT      540

TGGAAGTNGA TGAAANAATG TTTTA                                           565
```

(2) INFORMATION FOR SEQ ID NO:14:

(i) SEQUENCE CHARACTERISTICS:
        (A) LENGTH: 188 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
        (A) ORGANISM: Arabidopsis thaliana (vii) IMMEDIATE SOURCE:
        (B) CLONE: pKLU81

(xi) SEQUENCE DESCRIPTION: SEQ ID NO:14:

```
Leu Ser Gly Lys Ser Leu Val Xaa Ser Thr Ser Leu Phe Leu Thr Gly
 1               5                  10                  15
Ser Gly Ser Ser Ser Leu Ser Met His Thr Asn Asn Val Leu Ser Val
            20                  25                  30
```

```
Ser Leu Xaa Phe Arg Arg Asp Lys Thr Val Leu Trp Asn Arg Thr Trp
         35                  40                  45

Trp Arg Leu Xaa Phe Leu Ala Lys Asn Ile Cys Cys Ser Leu Pro Phe
     50                  55                  60

Xaa Phe Xaa Xaa Ser Ser Ile Tyr Lys Ala Lys Arg Ser Leu Cys Gly
 65              70                  75                      80

Cys Thr Cys Asp Lys Xaa Gly Ile Leu Met Thr Gly Ser Asn Gln Pro
                 85                  90                  95

Ala Val Glu Phe Arg Xaa Cys Asp Ile Cys Gly Met Gln Ser Glu Ser
                100                 105                 110

Ser Phe Thr Glu Glu Leu Cys Gly Val Thr Leu Val Xaa Thr Cys Asn
            115                 120                 125

Arg Xaa Xaa Val Leu Arg Ala Ser Gln Met Cys Gly Arg Thr Ser Leu
    130                 135                 140

Ser Arg Xaa Phe Ile Ser Ile Xaa Xaa Leu Leu Tyr Lys Cys Phe Thr
145                 150                 155                 160

Met Xaa Xaa Phe Xaa Gly Tyr Phe Phe Thr Ala Val Gly His Pro Xaa
                165                 170                 175

Leu Gly Ser Ile Trp Lys Xaa Met Lys Xaa Cys Phe
            180                 185
```

(2) INFORMATION FOR SEQ ID NO:15:

(i) SEQUENCE CHARACTERISTICS:
        (A) LENGTH: 355 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (A) LIBRARY: 1 FixII
        (B) CLONE: pKLU81

(xi) SEQUENCE DESCRIPTION: SEQ ID NO:15:

```
TGCCCCCTGG ATGGCATGTG GTGCTTGGAG GGTTGTGGTT GCAAACGTGA CAGGCCGTAC      60

ATGCACTGTC CACGTAAGTT CCGCTTACAA AAAATTTGGT TGTACAAGCA ATACAGAGAG     120

TAAGAGTACA CATCTCGATG ACTTACCTGC TGTGATTTAA TATTTCAGAT ATACCGAGAA     180

GTTGAAACTC CTGGAAGAAA CAGTTTAATC TACCACTCAA TAACCAAGAA GGGACCTTTG     240

CATGAAACCC CAATCAGTGA TCAATATAAG CCCCTGGGAT ATCTCGACAG CAACGTTTA     300

GCAGCAAGGA GGAGTAACAC TACTTATTGC TATGACTTCC CGTTGGTTTG TTACT         355
```

(2) INFORMATION FOR SEQ ID NO:16:

(i) SEQUENCE CHARACTERISTICS:
        (A) LENGTH: 118 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
            (A) ORGANISM: Arabidopsis thaliana (vii) IMMEDIATE SOURCE:
            (A) LIBRARY: 1 FixII
            (B) CLONE: pKLU81

(xi) SEQUENCE DESCRIPTION: SEQ ID NO:16:

Cys Pro Leu Asp Gly Met Trp Cys Leu Glu Gly Cys Gly Cys Lys Arg
 1               5                  10                  15

Asp Arg Pro Tyr Met His Cys Pro Arg Lys Phe Arg Leu Gln Lys Ile
                20                  25                  30

Trp Leu Tyr Lys Gln Tyr Arg Glu Xaa Glu Tyr Thr Ser Arg Xaa Leu
            35                  40                  45

Thr Cys Cys Asp Leu Ile Phe Gln Ile Tyr Arg Glu Val Glu Thr Pro
        50                  55                  60

Gly Arg Asn Ser Leu Ile Tyr His Ser Ile Thr Lys Lys Gly Pro Leu
65                  70                  75                  80

His Glu Thr Pro Ile Ser Asp Gln Tyr Lys Pro Leu Gly Tyr Leu Asp
                85                  90                  95

Arg Gln Arg Leu Ala Ala Arg Arg Ser Asn Thr Thr Tyr Cys Tyr Asp
               100                 105                 110

Phe Pro Leu Val Cys Tyr
            115

(2) INFORMATION FOR SEQ ID NO:17:

(i) SEQUENCE CHARACTERISTICS:
            (A) LENGTH: 172 amino acids
            (B) TYPE: amino acid
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: Arabidopsis thaliana (vii) IMMEDIATE SOURCE:
            (B) CLONE: pKLU81

(xi) SEQUENCE DESCRIPTION: SEQ ID NO:17:

Arg Pro Tyr Phe Leu Gln Ala Ala Val Pro Leu Leu Tyr Pro Cys Thr
 1               5                  10                  15

Arg Ile Met Tyr Cys Leu Phe Leu Phe Asn Phe Val Glu Ile Arg Arg
                20                  25                  30

Phe Tyr Gly Ile Glu His Gly Gly Gly Tyr Asp Ser Trp Arg Lys Thr
            35                  40                  45

Ser Val Val Ala Phe Pro Phe Asp Phe Asp Lys Ala Gln Ser Ile Arg
        50                  55                  60

Pro Lys Gly His Cys Val Ala Val Arg Val Thr Ser Glu Xaa Pro Asp
65                  70                  75                  80

Asp Gly Phe Lys Pro Thr Ser Gly Arg Val Gln Val Met Glx Tyr Leu
                85                  90                  95

Trp Asn Ala Lys Glx Lys Phe Ile His Glx Gly Thr Leu Trp Gly Asn
               100                 105                 110

Thr Cys Met Asn Leu Gln Gln Xaa Leu Ser Phe Lys Ser Lys Pro Asn
           115                 120                 125

```
Val Trp Ala Tyr Phe Ser Val Lys Val Ile Tyr Ile Tyr Xaa Xaa Ser
    130                 135                 140

Ala Ile Glx Val Phe His Asn Xaa Leu Ile Xaa Arg Leu Leu Phe Tyr
145                 150                 155                 160

Ser Cys Gly Ala Pro Xaa Ser Trp Phe His Leu Glu
                165                 170
```

(2) INFORMATION FOR SEQ ID NO:18:

(i) SEQUENCE CHARACTERISTICS:
        (A) LENGTH: 169 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Rattus rattus (xi) SEQUENCE DESCRIPTION: SEQ ID NO:18:

```
Pro Arg Leu Gln Val Glu His Pro Cys Thr Glu Met Val Ala Asp Val
  1                 5                  10                  15

Asn Leu Pro Ala Ala Gln Leu Gln Ile Ala Met Gly Ile Pro Leu Phe
                 20                  25                  30

Arg Ile Lys Asp Ile Arg Met Met Tyr Gly Val Ser Pro Trp Gly Asp
             35                  40                  45

Ala Pro Ile Asp Phe Glu Asn Ser Ala His Val Pro Cys Pro Arg Gly
 50                  55                  60

His Val Ile Ala Ala Arg Ile Thr Ser Glu Asn Pro Asp Glu Gly Phe
 65                  70                  75                  80

Lys Pro Ser Ser Gly Thr Val Gln Glu Leu Asn Phe Arg Ser Asn Lys
                 85                  90                  95

Asn Val Trp Gly Tyr Phe Ser Val Ala Ala Ala Gly Leu His Glu
                100                 105                 110

Phe Ala Asp Ser Gln Phe Gly His Cys Phe Ser Trp Gly Glu Asn Arg
            115                 120                 125

Glu Glu Ala Ile Ser Asn Met Val Val Ala Leu Lys Glu Leu Ser Ile
130                 135                 140

Arg Gly Asp Phe Arg Thr Thr Val Glu Tyr Leu Ile Lys Leu Leu Glu
145                 150                 155                 160

Thr Glu Ser Phe Gln Leu Asn Arg Ile
                165
```

(2) INFORMATION FOR SEQ ID NO:19:

(i) SEQUENCE CHARACTERISTICS:
        (A) LENGTH: 120 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Gallus domesticus (xi) SEQUENCE DESCRIPTION: SEQ ID NO:19:

Ala Ala Gln Leu Gln Ile Ala Met Gly Ile Pro Leu His Arg Ile Lys
1               5                   10                  15

Asp Ile Arg Val Met Tyr Gly Val Ser Pro Trp Gly Asp Gly Ser Ile
                20                  25                  30

Asp Phe Glu Asn Ser Ala His Val Pro Cys Pro Arg Gly His Val Ile
            35                  40                  45

Ala Ala Arg Ile Thr Ser Glu Asn Pro Asp Glu Gly Phe Lys Pro Ser
        50                  55                  60

Ser Gly Thr Val Gln Glu Leu Asn Phe Arg Ser Asn Lys Asn Val Trp
65                  70                  75                  80

Gly Tyr Phe Ser Val Ala Ala Ala Gly Gly Leu His Glu Phe Ala Asp
                85                  90                  95

Ser Gln Phe Gly His Cys Phe Ser Trp Gly Glu Asn Arg Glu Glu Ala
            100                 105                 110

Ile Ser Asn Met Val Val Ala Leu
        115                 120

(2) INFORMATION FOR SEQ ID NO:20:

(i) SEQUENCE CHARACTERISTICS:
        (A) LENGTH: 75 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Arabidopsis thaliana (vii) IMMEDIATE SOURCE:
        (A) LIBRARY: 1 FixII
        (B) CLONE: pKLS2

(xi) SEQUENCE DESCRIPTION: SEQ ID NO:20:

Ile Val Asp Ile Ala Glu Arg Ala Asp Val Asp Ala Val Trp Ala Gly
1               5                   10                  15

Trp Gly His Ala Ser Glu Asn Pro Leu Leu Pro Glu Lys Leu Ser Gln
                20                  25                  30

Ser Lys Arg Lys Val Ile Phe Ile Gly Pro Pro Gly Asn Ala Met Arg
            35                  40                  45

Ser Leu Gly Asp Lys Ile Ser Ser Thr Ile Val Ala Gln Ser Ala Lys
        50                  55                  60

Val Pro Cys Ile Pro Trp Ser Gly Thr Gly Val
65                  70                  75

(2) INFORMATION FOR SEQ ID NO:21:

(i) SEQUENCE CHARACTERISTICS:
        (A) LENGTH: 73 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:

(A) ORGANISM: Saccharomyces cerevisiae (xi) SEQUENCE DESCRIPTION: SEQ ID NO:21:

Cys Val Gln Met Ala Glu Val Thr Arg Val Asp Ala Val Trp Pro Gly
 1               5                  10                  15

Trp Gly His Ala Ser Glu Asn Pro Glu Leu Pro Asp Ala Leu Asp Ala
                20                  25                  30

Lys Gly Ile Ile Cys Leu Gly Pro Pro Ala Ser Ser Met Ala Ala Leu
            35                  40                  45

Gly Asp Lys Ile Gly Ser Ser Leu Ile Ala Gln Ala Ala Asp Val Pro
        50                  55                  60

Thr Leu Pro Trp Ser Gly Ser His Val
65                  70

(2) INFORMATION FOR SEQ ID NO:22:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Arabidopsis thaliana (vii) IMMEDIATE SOURCE:
        (A) LIBRARY: 1 FixII
        (B) CLONE: pKLS2

(xi) SEQUENCE DESCRIPTION: SEQ ID NO:22:

Arg Tyr Leu Val Ser Asp Asn Ser Asn Ile Asp Ala Asp Thr Pro Tyr
 1               5                  10                  15

Ala Glu Val Glu Val Met Lys Met Cys Met Pro Leu Leu Ser Pro Ala
                20                  25                  30

(2) INFORMATION FOR SEQ ID NO:23:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Saccharomyces cerevisiae (xi) SEQUENCE DESCRIPTION: SEQ ID NO:23:

Lys Phe Leu Val Glu Asn Gly Glu His Ile Ile Lys Gly Gln Pro Tyr
 1               5                  10                  15

Ala Glu Ile Glu Val Met Lys Met Gln Met Pro Leu Val Ser Gln Glu
                20                  25                  30

(2) INFORMATION FOR SEQ ID NO:24:

(i) SEQUENCE CHARACTERISTICS:
        (A) LENGTH: 692 base pairs
        (B) TYPE: nucleic acid

```
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Arabidopsis thaliana (vii) IMMEDIATE SOURCE:
          (A) LIBRARY: lambda FixII
          (B) CLONE: pKLS2

(xi) SEQUENCE DESCRIPTION: SEQ ID NO:24:

TCGACTCGAT CTGAAAATAT CTAGTGTTCA ACAAACTTCA GATTCTTCGA TCTACATATA      60

AATCTGTTAC ATTCTTTTTT TTATCAAAGA AATCACATTA TTTTAGTAAC TAATCCTAAC     120

TATAAAATCT TTATTCAAGT ATTTGATTAT CCTTGATGAA CTTTTAACAA ACGGAATCAA     180

ATATAGGAAA CTAAATCGAC CTATACAGAA AAATAATATT TAAATACAAT ACTTTTTTTT     240

CCTACTTAGC ACTTGGATGG CTTTATTGGC TTCATGATCT AGTGGAGCAA GATCAGTAGA     300

GATTTGATAT GGTTCAAGTT TGTTCTGGTC TAGTTTTTAC GGGCATTTTT ATGTACCTCG     360

TGAACTTTCA AGTTATAAAA TCCCGGTGCC TTGGAAAAAA AAGGTCTCAA AGACATAAGC     420

ATACAATAAA ATTTGTTTTA CAAAGTTTGG AACAAGTCAA CGATGATTCG TTAATTTTCA     480

TTGCTAAAAT GATTGGATCA TTCACAATTA ACAAAAATGA GGAAAGAATG AGAGAAAGAT     540

GATAAGGTTG CCATACAATA TAAACCCATA CCTAACTCTC AACTATATCT CAACCCCCAG     600

TCATTTATAG TTACTATTAA GCCATTAATA TTATTTCTTT GTCAATGAGA CCACTTTTAT     660

TCTCATTTTA AATAATCAAA CAAAATGAAG AT                                   692

(2) INFORMATION FOR SEQ ID NO:25:

(i) SEQUENCE CHARACTERISTICS:
        (A) LENGTH: 395 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Arabidopsis thaliana (vii) IMMEDIATE SOURCE:
          (B) CLONE: pKLS2

(xi) SEQUENCE DESCRIPTION: SEQ ID NO:25:

GAACTACTAT TATCTGAATT AACCGTGTTT TACTGTACAG AACACATGTA TTAAGCTCAA      60

TTTCAGCAAT GAAGTTTTGG TCTTTGGAGT TATTTGTCAT TCATCTGAAC ATCTTTGTCT     120

ACAACCTGTG TGCAGATGGC TGAAGTAACA CGCGTGGATG CAGTTTGGCC TGGTTGGGGT     180

CATGCATCTG AAAACCCCGA ATTACCTGAT GCCCTAGATG CAAAAGGAAT CATATGTCTT     240

GGTCCTCCAG CATCTTCAAT GGCAGCACTG GGAGATAAGA TTGGTTCTTC GTTGATTGCA     300

CAAGCTGCTA TGTACCCAC TCTGCCATGG AGTGGTTCCC ATGTAAGTAA ATTTACTCTT     360

GTTAAGCTTG AGTATTCTAT AGTGTCACCT AAATA                                395
```

(2) INFORMATION FOR SEQ ID NO:26:

(i) SEQUENCE CHARACTERISTICS:
        (A) LENGTH: 872 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (B) CLONE: pKLS2

(xi) SEQUENCE DESCRIPTION: SEQ ID NO:26:

```
GGAGGGTCCA ATTACTGTGC TCCGCCAGAA ACTTTTCAAG AAACTTGAAC AAGCAGCTAG      60
AAGGTTGGCT AAGAGTGTTA ACTATGTTGG AGCTGCTACT GTTGAGTATC TCCACAGTAT     120
GGACACTGGG GAGTACTACT TCTTAGAGCT TAACCCTCGC TTACAGGGTG GTTTCATACT     180
GCAGCTTTTT GCGTTGAAAT ATAATGAAGG TCCGGACTTG AAAATTGAAT GACTTGTTTA     240
ACTTGATGTT TGAGGTCAGG TTGAGCATCC TGTCACTGAG TGGATTGCCG AGATAAATCT     300
TCCTTCTGCC CAAGATATAC TGTGGGGATG GGAATTCCTC TCTGGCAAAT CCCTGGTATA     360
ATCTACGTCC TTATTTCTTA CAGGCAGCGG TTCCTCTTCT TTATCCATGC ACACGAATAA     420
TGTACTGTCT GTTTCTCTTT AATTTCGTAG AGATAAGACG GTTCTATGGA ATAGAACATG     480
GTGGAGGTTA TGATTCTTGG CGAAAAACAT CTGTTGTAGC CTTCCCTTTT GATTTTGATA     540
AAGCTCAATC TATAAGGCCA AAAGGTCATT GTGTGGCTGT ACGTGTGACA AGTGAGGATC     600
CTGATGACGG GTTCAAACCA ACCAGCGGTA GAGTTCAGGT AATGTGATAT CTGTGGAATG     660
CAAAGTGAAA GTTCATTCAC TGAGAACTCT GTGGGTAACA CTTGTATGAA CTTGCAACAG     720
GAGTTGAGTT TTAAGAGCAA GCCAAATGTG TGGGCGTACT TCTCTGTCAA GGTAATTATA     780
TCTATAGAGA CTCTGCTATA TAAGTGTTTC ACAATGTTTT AAATTTTACG ACTACTTTTT     840
TACAGTCTGG TGGAGGCATC CACGAGTTCT CG                                   872
```

(2) INFORMATION FOR SEQ ID NO:27:

(i) SEQUENCE CHARACTERISTICS:
        (A) LENGTH: 1641 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (B) CLONE: pKLS2

(xi) SEQUENCE DESCRIPTION: SEQ ID NO:27:

```
CTATGTAAGA ACCTCTTTCT CAGAGATTTA TTTGTCTTGA AAAGTTTCTA TCTGGTGACG      60
AAATGTTCTA TCTGTCCAGA AAGCATCAGC GACCAGTGCT GCTGTGGTTT CAGATTACGT     120
```

```
TGGTTATCTG GAGAAGGGGC AAATCCCTCC AAAGGTAATC CAATACCAGG GATCTCTTTT      180

GCCTTTCTAG TGATGTTCTT GTAGCTAACT TTTTCTCTCT TAACTTGCAG CATATATCTC      240

TTGTACATTC TCAAGTGTCT CTGAATATTG AAGGAAGTAA ATATACGGTA TTCGCCTACT      300

ATCCAAATTT TACGTCTCTG CAATTTCGTA TTTTCCTCTG CCATATTATT TTTGCGCTGA      360

AGATATTGTT ACCAGGCTTA CTAACATGAA CATAACTGTT CTAGAGTGAT TAGCAATGTA      420

GTCCGGGGTG GATCAGGAAC CTACAGGCTA AGAATGAACA AGTCAGAAGT GGTAGCAGAA      480

ATACACACTC TACGTGATGG AGGTCTGTTG ATGCAGGCAA GTTTTCTGCC TTTTTCTATA      540

CTACAAGACA AGGACATACA TGTGTCGCGC AGAAAAAAAC TTCTGGAGAA TCTCACTTCC      600

TTTTCTTGTT TTCACTGTCA TTGCAGTTGG ATGGCAAAAG CCATGTGATA TATGCAGAGG      660

AAGAAGCTGC AGGAACTCGT CTTCTCATTG ATGGAAGAAC TTGTTTGCTA CAGGTTTCTG      720

CTAATTTTTT TGTGTGTTTA CCATTTTACT TCACGTTTCT CTGAAGTCAT CTTTAGCTTT      780

TAAGCTGTCT GTCAATTTTG GCTTATTCAG AATGACCATG ATCCATCAAA GTTAATGGCT      840

GAGACACCGT GCAAGTTGAT GAGGTATTTG GTTTCTGACA ACAGCAATAT TGACGCTGAT      900

ACGCCTTATG CCGAAGTTGA GGTCATGAAG ATGTGCATGC CACTTCTTTC ACCTGCTTCA      960

GGAGTTATCC ATCTTAAAAT GTCTGAAGGA CAAGACATGC AGGTTCACTT CATTGCTAAA     1020

CAAAAAGTCT ACAGTTCTGT TTAAATTGAT TAACCCATCC ATTATTTTTT TCACAGGCTG     1080

GTGAACTTAT CGCCAATCTT GATCTTGATG ATCCTTCTGC TGTAAGAAAG GCCGAACCCT     1140

TCCATGGAAG TTTCCCAAGA TTAGGGCTTC CAACTGCAAT ATCCGGTAGA GTTCATCAGA     1200

GATGTGCCGC AACATTAAAT GCTGCACGCA TGATTCTTGC TGGCTATGAG CATAAAGTAG     1260

ATGAGGTAAA CACTGTTTGT TTTTCCTATT TGATCCAACT CTCTCTACTA GATTATTTGA     1320

CTATGAGATA GCTCATACGT CGCAGGTTGT TCAAAGACTT ACTTAATTGC CTTGATAGCC     1380

CTGAACTCCC ATTTCTTGCA GTGGCAACAG TGCTTTGCAG TTCTGGCGAC ACGACTACCT     1440

AAAAATCTCA GGAACATGGT AAACACCTGT GTAGTATTCA TAATCCGGTT CTTATATATT     1500

GATATTTGTT TTGAGTTCAA GACTTTTAAT CATATCTAAA TAAAACTCTT TATCAGCTAG     1560

AATCAAAGTA TAGGGAATTT GAGAGTATTT CCAGAAACTC TTTGACCACC GATTTCCCTG     1620

CCAAACTTTT AAAAGGCAGT C                                                1641

(2) INFORMATION FOR SEQ ID NO:28:

(i) SEQUENCE CHARACTERISTICS:
        (A) LENGTH: 725 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (B) CLONE: pKLS2

(xi) SEQUENCE DESCRIPTION: SEQ ID NO:28:

CGAGTCAATT ACTTGAACAG ACCAAACTAA GTGAAGCTTC GTTCAAACAT TGCTAGAAGC       60

CTTTCAGAGT TAGAAATGTT TACAGAGGAC GGAGAAAATA TGGATACTCC CAAGAGGAAA      120
```

```
AGTGCCATTA ATGAAAGAAT AGAAGATCTT GTAAGCGCAT CTTTAGCTGT TGAAGACGCT      180

CTCGTGGGAC TATTTGACCA TAGCGATCAC ACACTTCAAA GACGGGTTGT TGAGACTTAT      240

ATTCGCAGAT TATACCAGGT TCGAGTTCAT TCTTCCGCAC CCTTATTGTT CAAAATTCTT      300

TTTGTACTGC AATTGATTAC AGAAAATTTT GACTTCATTT TAACCCGACT CTTGTCATCA      360

GCCCTACGTC GTTAAAGATA GCGTGAGGAT GCAGTCGCGC CGGATGCAGT GGCACCTTTC      420

TGGTCTTCTT GATTCCTGGG ATTTCCTAGA GGAGCATATG GAAAGAAAAA ACATTGGTTT      480

AGACGATCAC GACACATCTG AAAAAGGATT GGTTGAGAAG CGTAGTAAGA GAAAATGGGG      540

GGCTATGGTT ATAATCAAAT CTTTGGAGTT TCTTCCACGT ATAATACGTG CAGCATTGAG      600

AGAAACATAG CACAACGACT ATGAAACTGC CGGAGCTCCT TTATCTGGCA ATATGATGCA      660

CATTGCTATT GTCGGGCATC AACAACCAGA TGAGTCTGCT TCAGGACAGG TACTTGACAC      720

AGTAT                                                                 725
```

(2) INFORMATION FOR SEQ ID NO:29:

(i) SEQUENCE CHARACTERISTICS:
        (A) LENGTH: 830 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (B) CLONE: pKLS2 - Region E (xi) SEQUENCE DESCRIPTION: SEQ ID NO:29:

```
ACCGAGAAGT GAACCTGAAG AAACAGTTTA ATCTACCACT CAATAACCCA AGAAGGGACC       60

TTTGCATGAA ACCCCAATCA GTGATCAATA TAAGCCCCTG GGATATCTCG ACAGGCAACG      120

TTTAGCAGCA AGGAGGAGTA ACACTACTTA TTGCTATGAC TTCCCGTTGG TTTGTTACTG      180

AATTCATAAG ATTCACACAT ACGCTTACTC TTTTGGCTAT TTCCAACCCC CCTTATGTTA      240

TTTCTTTCCT TTTCAGGCAT TTGGGACAGC CTTGGAACTG TTGTGGGCAT CACAACACCC      300

AGGAGTTAAG AAACCATATA AGGATACTCT GATCAATGTT AAAGAGCTTG TATTCTCAAA      360

ACCAGAAGGT TCTTCGGGTA CATCTCTAGA TCTGGTTGAA AGACCACCCG GTCTCAACGA      420

CTTTGGAATG GTTGCCTGGT GCCTAGATAT GTCGACCCCA GAGTTTCCTA TGGGGCGGAA      480

ACTTCTCGTG ATTGCGAATG ATGTCACCTT CAAAGCTGGT TCTTTTGGTC CTAGAGAGGA      540

CGCGTTTTTC CTTGCTGTTA CTGAACTCGC TTGTGCCAAG AAGCTTCCCT TGATTTACTT      600

GGCAGCAAAT TCTGGTGCCC GACTTGGGGT TGCTGAAGAA GTCAAAGCCT GCTTCAAAGT      660

TGGATGGTCG GATGAAATTT CCCCTGAGAA TGGTTTTTCA GTATATATAC CTAAGCCCTG      720

AAGACCACGA AAGGATTGGT CATCTGTCAT TTGCCCATGA AGGTAAAGCT CCCTAGTGGG      780

GGAAACTAGG GTGGGGTGAA TTGATACGGT CGTTGGGCAA AGAAGGATGG                 830
```

(2) INFORMATION FOR SEQ ID NO:30:

(i) SEQUENCE CHARACTERISTICS:
        (A) LENGTH: 764 base pairs

```
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (B) CLONE: pKLS2 - Region F (xi) SEQUENCE DESCRIPTION: SEQ ID NO:30:

GCAAGCTCGA AATTAACCCT CACTAAAGGG AACAAAAGCT GGAGCTCTCT TGTAAAAAAC      60

GTAAGAGAAG CATCTGGAGA CAACTTAGCA TATAAATCTT CAATGCGTCT GATTCAGGAT     120

TGGTTCTGCA ACTCTGATAT TGCAAAGGGG AAAGAAGAAG CTTGGACAGA CGACCAAGTG     180

TTCTTTACAT GGAAGGACAA TGTTAGTAAC TACGAGTTGA AGCTGAGCGA GTTGAGAGCG     240

CAGAAACTAC TGAACCAACT TGCAGAGATT GGGAATTCCT CAGATTTGCA AGCTCTGCCA     300

CAAGGACTTG CTAATCTTCT AAACAGGGTA AAAACAAAA CCCCCCAAAA AAACAAGGTT      360

TTGGTCCCCA AGTAATCCTA ACCTGTATGC CGGTTTTTAA AGCCCTAAGT AAATATTTGT     420

GATGCAGGTG GACCGTCGAA AAAGAGAAGA GCTGGTGGCT GCTATTCGAA AGGTCTTGGG     480

TTGACTGATA TCGAAGACTT TAGCTTCTAA TCCAAGAAAG ATGGACATTT AAAGTTTGCT     540

TGTGTCCATT TGGACCATCT TCCTTATATT TGTTGGTCAC AGTTGTAAAT GTTGTTGTAG     600

CTTTGTCATT TCCGTATAAA CAAATTACGC AATAATTCAT TCAACATGTC ACTCTTGCTT     660

CATATTTATA CACTGAACCA AGACAATATA ATAGTCTAAA TATAAAACTG ATCGGTCGAC     720

GCCCTATAGT GAGTCGTATT AAGCCGGCCG CGAGCTCTAG AGTC                     764

(2) INFORMATION FOR SEQ ID NO:31:

(i) SEQUENCE CHARACTERISTICS:
        (A) LENGTH: 796 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Brassica napus
        (D) DEVELOPMENTAL STAGE: Embryo (ix) FEATURE:
        (A) NAME/KEY: Binding-site
        (B) LOCATION: 388..392

(xi) SEQUENCE DESCRIPTION: SEQ ID NO:31:

Ala Gly Arg Arg Leu Ala Lys Ser Val Asn Tyr Val Gly Ala Ala Thr
 1               5                  10                  15

Val Glu Tyr Leu Tyr Ser Met Asp Thr Gly Glu Tyr Tyr Phe Leu Glu
            20                  25                  30

Leu Asn Pro Arg Leu Gln Val Glu His Pro Val Thr Glu Trp Ile Ala
        35                  40                  45
```

-continued

```
Glu Ile Asn Leu Pro Ala Ala Gln Val Ala Val Gly Met Gly Ile Pro
 50                  55                  60
Leu Trp Gln Ile Pro Glu Ile Arg Arg Phe Tyr Gly Ile Glu His Gly
 65                  70                  75                  80
Gly Gly Tyr Asp Ser Trp Arg Lys Thr Ser Val Leu Ala Ser Pro Phe
                 85                  90                  95
Asp Phe Asp Lys Ala Glu Ser Ile Arg Pro Lys Gly His Cys Val Ala
            100                 105                 110
Val Arg Val Thr Ser Glu Asp Pro Asp Gly Phe Lys Pro Thr Ser
        115                 120                 125
Gly Lys Val Gln Glu Leu Ser Phe Lys Ser Lys Pro Asn Val Trp Ala
    130                 135                 140
Tyr Phe Ser Val Lys Ser Gly Gly Ile His Glu Phe Ser Asp Ser
145                 150                 155                 160
Gln Phe Gly His Val Phe Ala Phe Gly Glu Ser Arg Ala Leu Ala Ile
                165                 170                 175
Ala Asn Met Val Leu Gly Leu Lys Lys Asn Gln Asn Arg Gly Lys Ile
            180                 185                 190
Arg Thr Asn Val Asp Tyr Thr Ile Asp Leu Leu His Ala Ser Asp Tyr
        195                 200                 205
Arg Glu Asn Gln Ile His Thr Gly Trp Leu Asp Ser Arg Ile Ala Met
    210                 215                 220
Arg Val Arg Ala Glu Arg Pro Pro Trp Tyr Leu Ser Val Val Gly Gly
225                 230                 235                 240
Ala Leu Tyr Lys Ala Ser Ala Thr Ser Ala Ala Val Val Ser Asp Tyr
                245                 250                 255
Val Gly Tyr Leu Glu Lys Gly Gln Ile Pro Pro Lys His Ile Ser Leu
            260                 265                 270
Val His Ser Gln Val Ser Leu Asn Ile Glu Gly Ser Lys Tyr Thr Ile
        275                 280                 285
Asp Val Val Arg Gly Gly Ser Gly Ser Tyr Arg Leu Arg Met Asn Asn
    290                 295                 300
Ser Glu Val Val Ala Glu Ile His Thr Leu Arg Asp Gly Gly Leu Leu
305                 310                 315                 320
Met Gln Leu Asp Gly Lys Ser His Val Ile Tyr Ala Glu Glu Ala
                325                 330                 335
Ala Gly Thr Arg Leu Leu Ile Asp Gly Arg Thr Cys Leu Leu Gln Asn
            340                 345                 350
Asp His Asp Pro Ser Lys Leu Met Ala Glu Thr Pro Cys Lys Leu Leu
        355                 360                 365
Arg Tyr Leu Val Ser Asp Asn Ser Ser Ile Asp Ala Asp Met Pro Tyr
    370                 375                 380
Ala Glu Val Glu Val Met Lys Met Cys Met Pro Leu Leu Ser Pro Ala
385                 390                 395                 400
Ser Gly Val Ile His Phe Lys Met Ser Glu Gly Gln Ala Met Gln Ala
                405                 410                 415
Gly Glu Leu Ile Ala Lys Leu Asp Leu Asp Asp Pro Ser Ala Val Arg
            420                 425                 430
Lys Ala Glu Pro Phe His Gly Gly Phe Pro Arg Leu Gly Leu Pro Thr
        435                 440                 445
Ala Ile Ser Gly Lys Val His Gln Arg Cys Ala Ala Thr Leu Asn Ala
    450                 455                 460
```

```
Ala Arg Met Val Leu Ala Gly Tyr Glu His Lys Val Asp Glu Val Val
465                 470                 475                 480

Gln Asp Leu Leu Asn Cys Leu Asp Ser Pro Glu Leu Pro Phe Leu Gln
                485                 490                 495

Trp Gln Glu Cys Phe Ala Val Leu Ala Thr Arg Leu Pro Lys Asp Leu
            500                 505                 510

Arg Met Met Leu Glu Ser Lys Tyr Arg Glu Phe Glu Ser Ile Ser Arg
        515                 520                 525

Asn Ser Leu Thr Ala Asp Phe Pro Ala Lys Leu Leu Lys Gly Ile Leu
530                 535                 540

Glu Ala His Leu Leu Ser Cys Asp Glu Lys Asp Arg Gly Ala Leu Glu
545                 550                 555                 560

Arg Leu Ile Glu Pro Leu Met Ser Leu Ala Lys Ser Tyr Glu Gly Gly
                565                 570                 575

Arg Glu Ser His Ala Arg Val Ile Val His Ser Leu Phe Glu Glu Tyr
            580                 585                 590

Leu Ser Val Glu Glu Leu Phe Asn Asp Asn Met Leu Ala Asp Val Ile
        595                 600                 605

Glu Arg Met Arg Gln Gln Tyr Lys Lys Asp Leu Leu Lys Ile Val Asp
610                 615                 620

Ile Val Leu Ser His Gln Gly Ile Lys Asp Lys Asn Lys Leu Val Leu
625                 630                 635                 640

Arg Leu Met Glu Gln Leu Val Tyr Pro Asn Pro Ala Ala Tyr Arg Asp
                645                 650                 655

Lys Leu Ile Arg Phe Ser Thr Leu Asn His Thr Asn Tyr Ser Glu Leu
            660                 665                 670

Ala Leu Lys Ala Ser Gln Leu Leu Glu Gln Thr Lys Leu Ser Glu Leu
        675                 680                 685

Pro Ala Ser Asn Ile Ala Arg Ser Leu Ser Glu Leu Glu Met Phe Thr
690                 695                 700

Glu Asp Gly Glu Asn Met Asp Thr Pro Lys Arg Lys Ser Ala Ile Asn
705                 710                 715                 720

Glu Arg Met Glu Asp Leu Val Ser Ala Ser Leu Ala Val Glu Asp Ala
                725                 730                 735

Leu Val Gly Leu Phe Asp His Ser Asp His Thr Leu Gln Arg Arg Val
            740                 745                 750

Val Glu Thr Tyr Ile Arg Arg Leu Tyr Gln Pro Tyr Val Val Lys Glu
        755                 760                 765

Ser Ile Arg Met Gln Trp His Arg Ser Gly Leu Ile Ala Ser Trp Glu
770                 775                 780

Phe Leu Glu Glu His Ile Phe Arg Lys His Trp Leu
785                 790                 795
```

(2) INFORMATION FOR SEQ ID NO:32:

(i) SEQUENCE CHARACTERISTICS:
        (A) LENGTH: 2391 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:

(A) ORGANISM: Brassica napus
(D) DEVELOPMENTAL STAGE: Embryo (vii) IMMEDIATE SOURCE:
(B) CLONE: pRS6, pRS8

(xi) SEQUENCE DESCRIPTION: SEQ ID NO:32:

| | | | | | |
|---|---|---|---|---|---|
| TGGCTGGTAG | AAGGTTGGCT | AAGAGTGTTA | ACTATGTTGG | AGCAGCTACT | GTTGAATATC | 60 |
| TCTACAGCAT | GGACACGGGG | GAGTACTACT | TCTTAGAGCT | TAACCCTCGG | TTACAGGTTG | 120 |
| AGCACCCTGT | AACTGAATGG | ATTGCCGAGA | TAAATCTTCC | TGCTGCGCAA | GTTGCTGTTG | 180 |
| GGATGGGAAT | TCCTCTCTGG | CAAATCCCTG | AGATAAGACG | GTTCTATGGT | ATAGAACATG | 240 |
| GTGGAGGTTA | CGATTCTTGG | AGGAAAACAT | CTGTGCTAGC | CTCCCCTTTT | GATTTTGATA | 300 |
| AAGCTGAATC | TATAAGGCCA | AAAGGTCATT | GTGTGGCTGT | ACGCGTGACA | AGTGAGGACC | 360 |
| CTGATGACGG | ATTCAAACCC | ACCAGCGGTA | AAGTACAGGA | GTTGAGTTTT | AAAAGCAAGC | 420 |
| CAAATGTGTG | GGCTTACTTC | TCTGTCAAGT | CTGGTGGAGG | CATCCACGAG | TTCTCAGATT | 480 |
| CCCAATTTGG | CCATGTTTTT | GCATTTGGGG | AATCCAGAGC | CTTGGCAATA | GCAAATATGG | 540 |
| TCCTTGGGCT | AAAAAAAAT | CAAAATCGTG | GAAAAATTAG | GACTAACGTT | GACTACACGA | 600 |
| TTGACCTTTT | ACATGCTTCT | GATTACCGGG | AAAACCAAAT | TCACACTGGT | TGGTTGGACA | 660 |
| GTAGAATTGC | TATGCGGGTC | AGGGCAGAGA | GGCCTCCATG | GTACCTCTCT | GTTGTCGGAG | 720 |
| GGGCTCTCTA | TAAAGCATCA | GCGACCAGTG | CTGCTGTAGT | CTCGGATTAT | GTTGGTTATC | 780 |
| TAGAGAAGGG | ACAAATTCCC | CCAAAGCATA | TATCTCTTGT | GCATTCTCAA | GTGTCTCTGA | 840 |
| ACATTGAAGG | AAGTAAATAT | ACGATTGATG | TGGTCCGGGG | TGGATCAGGA | AGCTACAGGC | 900 |
| TAAGAATGAA | CAACTCAGAA | GTTGTAGCAG | AAATACACAC | TCTACGTGAT | GGAGGTCTGT | 960 |
| TGATGCAGTT | GGATGGTAAA | AGCCATGTGA | TATATGCAGA | GGAAGAAGCT | GCAGGAACCC | 1020 |
| GTCTTCTTAT | TGACGGAAGA | ACTTGTTTAC | TTCAGAATGA | TCACGATCCT | TCAAAGTTGA | 1080 |
| TGGCTGAGAC | ACCGTGCAAG | CTGCTGAGGT | ATTTGGTTTC | AGATAATAGC | AGTATTGATG | 1140 |
| CTGACATGCC | CTACGCGGAA | GTTGAGGTCA | TGAAGATGTG | CATGCCACTT | CTTTCACCTG | 1200 |
| CATCAGGAGT | TATACATTTC | AAAATGTCTG | AAGGACAAGC | CATGCAGGCT | GGTGAACTTA | 1260 |
| TAGCCAAGCT | TGATCTTGAT | GATCCTTCTG | CTGTAAGAAA | GGCCGAACCC | TTCCATGGAG | 1320 |
| GTTTCCCAAG | ATTAGGGCTT | CCAACGGCAA | TTTCTGGTAA | AGTTCATCAG | AGATGTGCTG | 1380 |
| CAACTTTAAA | TGCTGCTCGC | ATGGTTCTTG | CCGGCTATGA | GCATAAAGTA | GATGAGGTTG | 1440 |
| TTCAAGACTT | GCTTAACTGC | CTTGATAGCC | CTGAACTCCC | ATTCCTTCAG | TGGCAAGAGT | 1500 |
| GCTTCGCAGT | TCTGGCAACA | CGACTACCGA | AAGATCTCAG | AATGATGTTA | GAATCCAAGT | 1560 |
| ATAGGGAATT | TGAGAGTATA | TCCAGGAACT | CTCTCACCGC | AGATTTCCCT | GCCAAACTTT | 1620 |
| TAAAAGGCAT | TCTTGAGGCT | CATTTATTAT | CTTGTGATGA | GAAAGATAGG | GGTGCCCTTG | 1680 |
| AAAGGCTCAT | TGAACCATTG | ATGAGCCTTG | CAAAGTCTTA | TGAAGGTGGT | AGAGAAAGTC | 1740 |
| ATGCCCGTGT | TATTGTTCAT | TCTCTTTTTG | AAGAATACCT | ATCTGTAGAA | GAATTATTCA | 1800 |
| ATGATAACAT | GCTGGCTGAT | GTTATTGAAC | GCATGCGTCA | GCAATACAAG | AAAGATCTGT | 1860 |
| TGAAGATTGT | TGATATTGTG | CTCTCACACC | AGGGCATTAA | AGACAAAAAC | AAACTCGTTC | 1920 |
| TTCGGCTCAT | GGAGCAGCTT | GTTTACCCTA | ATCCTGCTGC | ATACAGAGAT | AAACTTATCC | 1980 |
| GATTCTCGAC | ACTAAACCAT | ACTAATTACT | CTGAGTTGGC | ACTGAAGGCA | AGCCAATTAC | 2040 |
| TCGAACAGAC | CAAATTAAGT | GAACTTCCAG | CTTCAAACAT | TGCTAGAAGC | CTGTCAGAGT | 2100 |
| TAGAAATGTT | TACAGAGGAT | GGGGAAAATA | TGGATACTCC | CAAGAGGAAG | AGTGCCATTA | 2160 |

-continued

```
ATGAAAGAAT GGAAGATCTT GTGAGCGCAT CCTTAGCTGT TGAAGATGCT CTCGTGGGAC    2220

TATTTGACCA CAGCGATCAC ACACTTCAAA GACGAGTTGT TGAGACTTAT ATTCGCAGAT    2280

TATATCAGCC CTACGTCGTC AAAGAAAGCA TCAGGATGCA ATGGCACCGG TCTGGTCTTA    2340

TTGCTTCTTG GGAGTTCCTA GAGGAGCATA TTTTCCGGAA ACATTGGCTT A            2391
```